(12) United States Patent
Sørensen et al.

(10) Patent No.: US 12,157,701 B2
(45) Date of Patent: Dec. 3, 2024

(54) BUILDING MATERIALS COMPRISING DIGESTATE

(71) Applicant: RENESCIENCE A/S, Fredericia (DK)

(72) Inventors: Hanne Risbjerg Sørensen, Holte (DK); Linda Kaare Nørskov, Søborg (DK)

(73) Assignee: RENESCIENCE A/S, Fredericia (DK)

( * ) Notice: Subject to any disclaimer, the term of this patent is extended or adjusted under 35 U.S.C. 154(b) by 1148 days.

(21) Appl. No.: 16/969,370

(22) PCT Filed: Feb. 11, 2019

(86) PCT No.: PCT/EP2019/053304
§ 371 (c)(1),
(2) Date: Jan. 11, 2021

(87) PCT Pub. No.: WO2019/158477
PCT Pub. Date: Aug. 22, 2019

(65) Prior Publication Data
US 2021/0130238 A1    May 6, 2021

(30) Foreign Application Priority Data
Feb. 13, 2018 (EP) .................................... 18156484

(51) Int. Cl.
| C04B 33/04 | (2006.01) |
| C04B 33/132 | (2006.01) |
| C04B 33/135 | (2006.01) |
| C04B 33/30 | (2006.01) |
| C04B 33/32 | (2006.01) |

(52) U.S. Cl.
CPC .......... *C04B 33/1355* (2013.01); *C04B 33/04* (2013.01); *C04B 33/1325* (2013.01); *C04B 33/30* (2013.01); *C04B 33/32* (2013.01); *C04B 2235/349* (2013.01); *C04B 2235/606* (2013.01);
(Continued)

(58) Field of Classification Search
CPC ................ B09B 3/00; C04B 2235/349; C04B 2235/5427; C04B 2235/606; C04B 2235/65; C04B 2235/96; C04B 2235/9607; C04B 2235/9615; C04B 33/04; C04B 33/132; C04B 33/1325; C04B 33/1355;
(Continued)

(56) References Cited

U.S. PATENT DOCUMENTS

| 4,112,033 A | 9/1978 | Lingl |
| 2016/0115063 A1* | 4/2016 | Ronsch .................. C02F 11/04 435/167 |
| 2017/0306270 A1* | 10/2017 | Nielsen ................ C12N 9/2448 |

FOREIGN PATENT DOCUMENTS

| CN | 1757610 A | 4/2006 |
| CN | 103304217 A | 9/2013 |

(Continued)

OTHER PUBLICATIONS

English Machine Translation: CN 103304217A (Year: 2013).*
(Continued)

*Primary Examiner* — Holly Rickman
*Assistant Examiner* — Linda N Chau
(74) *Attorney, Agent, or Firm* — McNeill PLLC

(57) ABSTRACT

The present invention relates to a process for producing building materials, such as bricks, lightweight aggregates and concrete, which building materials comprise digestate obtained from municipal solid waste (MSW) which has been added one or more enzymes to liquefy the organic fraction of MSW.

20 Claims, 12 Drawing Sheets

(52) U.S. Cl.
CPC .. *C04B 2235/65* (2013.01); *C04B 2235/9615* (2013.01)

(58) Field of Classification Search
CPC ........... C04B 33/30; C04B 33/32; C12N 1/00; Y02P 40/60
See application file for complete search history.

(56) References Cited

FOREIGN PATENT DOCUMENTS

| | | |
|---|---|---|
| JP | 50-3422 A2 | 1/1975 |
| WO | WO 2007/036795 A1 | 4/2007 |
| WO | WO 2011/032557 A2 | 3/2011 |
| WO | WO 2013/018778 A1 | 2/2013 |
| WO | WO 2013/185777 A1 | 12/2013 |
| WO | WO 2014/198274 A1 | 12/2014 |
| WO | WO 2016/030472 A1 | 3/2016 |
| WO | WO 2016/050893 A1 | 4/2016 |
| WO | WO 2017/174093 A2 | 10/2017 |

OTHER PUBLICATIONS

Belmonte et al., "Screening of heavy metal containing waste types for use as raw material in Arctic clay-based bricks," Environ. Sci Pollut Res, 25: 32831-32843 (2018).
Chen et al., "Preparation of eco-friendly construction bricks from hematite tailings," Construction and Building Materials, 25(4): 2107-2111 (2011).
Chindaprasirt et al., "Comparative study on the characteristics of fly ash and bottom ash geopolymers," Waste Management, 29(2): 539-543 (2009).
Cultrone et al., "Influence of mineralogy and firing temperature on the porosity of bricks," Journal of the European Ceramic Society, 24(3): 547-564 (2004).
Demirboğa, "Influence of mineral admixtures on thermal conductivity and compressive strength of mortar," Energy and Buildings, 35(2): 189-192 (2003).
Donatello et al., "Comparison of test methods to assess pozzolanic activity," Cement & Concrete Composites, 32(2): 121-127 (2010).
Ducman et al., "The applicability of different waste materials for the production of lightweight aggregates," Waste Management, 29(8): 2361-2368 (2009).
Franus et al., "Utilization of sewage sludge in the manufacture of lightweight aggregate," Environ Monit Assess, 188(1): 10, 13 pages (2016).
Fu et al., "Effects of silica fume, latex, methylcellulose, and carbon fibers on the thermal conductivity and specific heat of cement paste," Cement and Concrete Research, 27(12): 1799-1804 (1997).

Ghosal et al., "Particle size-density relation and cenosphere content of coal fly ash," Fuel, 74(4): 522-529 (1995).
Goodarzi, "Characteristics and composition of fly ash from Canadian coal-fired power plants," Fuel, 85(10-11): 1418-1427 (2006).
Henry et al., "Compound Forms of Fossil Fuel Fly Ash Emissions," Environmental Science & Technology, 14(4): 450-456 (1980).
Hernández et al., "Thermal decomposition of sewage sludge under $N_2$, $CO_2$ and air: Gas characterization and kinetic analysis," Journal of Environmental Management, 196: 560-568 (2017).
Karius et al., "pH and grain-size variation in leaching tests with bricks made of harbour sediments compared to commercial bricks," The Science of the Total Environment, 278: 73-85 (2001).
Khokhar et al., "Mix design of concrete with high content of mineral additions: Optimisation to improve early age strength," Cement & Concrete Composites, 32(5): 377-385 (2010).
Kosmatka et al., "Design and Control of Concrete Mixtures: The guide to applications, methods, and materials," $15^{th}$ Edition, Portland Cement Association, 459 pages (2011).
Lee et al., "Effect of particle size distribution of fly ash—cement system on the fluidity of cement pastes," Cement and Concrete Research, 33(5): 763-768 (2003).
Moosberg-Bustnes et al., "The function of fillers in concrete," Materials and Structures, 37(266): 74-81 (2004).
Oner et al., "An experimental study on strength development of concrete containing fly ash and optimum usage of fly ash in concrete," Cement and Concrete Research, 35(6): 1165-1171 (2005).
Taurino et al. "New fired bricks based on municipal solid waste incinerator bottom ash," Waste Management & Research, 35: 1055-1063 (2017).
Torres et al., "Incorporation of wastes from granite rock cutting and polishing industries to produce roof tiles," Journal of the European Ceramic Society, 29(1): 23-30 (2009).
Tzouvalas et al., "Alternative calcium sulfate-bearing materials as cement retarders: Part I. Anhydrite," Cement and Concrete Research, 34(11): 2113-2118 (2004).
Wong et al., "Effects of Fly Ash on Yields and Elemental Composition of Two Vegetables, *Brassica parachinensis* and *B. chinensis*," Agriculture, Ecosystems & Environment, 30(3-4): 251-264 (1990).
Yue et al., "Properties and effect of forming sewage sludge into lightweight ceramics," Front. Environ. Sci. Engin., 6(1): 117-124 (2012).
Zevenbergen et al., "Clay Formation and Metal Fixation during Weathering of Coal Fly Ash," Environ. Sci. Technol., 33(19): 3405-3409 (1999).
A. Ghani, Search Report for Singaporean Patent Application No. 11202007709V, completed Sep. 8, 2021 (2 pages).
K.-C. Thienel et al., "Lightweight Concrete-From Basics to Innovations," Materials, 13(5): 1120, 24 pages (2020).

\* cited by examiner

BUILDING MATERIALS COMPRISING DIGESTATE

CROSS-REFERENCE TO RELATED APPLICATIONS

This application is a national stage filing under 35 U.S.C. 371 of PCT/EP2019/053304 filed Feb. 11, 2019, which International Application was published by the International Bureau in English on Aug. 22, 2019, and application claims priority from European Patent Application No. 18156484.0, filed Feb. 13, 2018, which applications are hereby incorporated in their entirety by reference in this application.

TECHNICAL FIELD

The present invention relates to methods for producing building materials, such as bricks, lightweight aggregates and concrete and the corresponding building materials.

BACKGROUND

Building materials such as bricks, tiles, lightweight aggregates, cement, concrete, and mortar are strong building materials made from e.g. clay and/or sand by a process where the raw materials and optionally water are mixed and shaped, then dried and optionally fired at conditions resulting in the building material.

Including waste materials, such as sludge, as a raw material in the manufacture of various building materials have received attention since this combines the recycling of the waste materials and the sustainable handling of environmental pollution problems and conserving pristine raw material resources. Waste materials and sludge typically comprise the main components organic matter, water and inorganic matter. In particular the content of water and organic matter is important when used as a raw material in the manufacture of building materials such as ceramic building materials. Ceramic building materials are strong materials and their properties as regards strength, water absorption etc. are important for their use in building structures.

U.S. Pat. No. 4,112,033 discloses a method for producing bricks or other ceramic articles from sewage sludge having environmentally harmful and/or toxic substances therein. The method includes the venting of exhaust air from the dryer into the kiln as combustion air to destroy aromatic compounds.

CN103304217 discloses a method for preparing ceramsite by utilizing sludge subjected to anaerobic digestion. The ceramic particles are prepared using the treated sludge as the main raw material, i.e. a very high proportion of sludge.

One challenge using sewage sludge as a component in building materials is to avoid colouring effects in e.g. bricks. Also, sewage sludge typically contains substantial proportions of phosphor which may hamper its use in e.g. concrete. Another disadvantage of sewage sludge is that lightweight aggregates may tend to shrink when sewage sludge is used as a raw material (Danish Standard Euronorm (DS-EN) 450-1, and Sigvardsen and Ottosen (2016), Proceedings of the 6th Int Conference on Waste Management and The Environment (VM2016)).

In the bricks industry, shrinkage during manufacturing is closely monitored to assure that the final brick size is well-defined and complies with standardized dimensions, irrespectively of the raw material mix used in the given production.

Drying shrinkage is defined as the contracting of a freshly moulded green brick due to the loss of capillary water by evaporation and the particles of clay body have formed as a stable framework. All clay bricks, when formed, contain water which must be removed during a drying stage, before the bricks can be fired. This process must be carefully controlled so as not to stress the brick, which could lead to distortion and cracking. The rate at which a brick dries is controlled by adjusting at least temperature, humidity and air movement. The movement of air, controlled by fans, is used to help evenly distribute the air around the product and remove saturated air.

Firing shrinkage happens at the vitrification stage of the process for manufacturing bricks. This is due to diminished size of the particles as they approach fusion and to the closer arrangement of particles in their glassy matrix. The purpose of firing bricks is to transform the relatively weak dried clay into strong, durable bricks. The firing of bricks is a complex subject, because of the large difference in the types of clay used, in the methods of manufacture, in the types of kiln used and in the types of products. During the firing process reactions occur within the clay body, some of which transform the unfired body and develop the fired properties. The effects of firing on a clay body include shrinkage, weight loss, increased strength and a change in colour.

There is a need for providing economical building materials having additions and fillers which are cheap and which do not compromise the quality of the building materials, e.g. strength, non-toxicity for recycling etc. Also, there is a need for providing sustainable solutions for recycling the waste derived digestate from Municipal Solid Waste (MSW) processes comprising liquefaction of the organic fraction of MSW by addition of one or more enzymes.

SUMMARY

In a first aspect the present invention provides a process for manufacture of a building material such as a ceramic building material comprising the steps of:
  mixing clay and/or sand with digestate obtained from a Municipal Solid Waste (MSW) process comprising liquefaction of the organic fraction of MSW by addition of one or more enzymes,
  optionally adjusting the water contents of the mixture,
  shaping the mixture,
  drying the shaped mixture, and
  optionally firing the shaped mixture,
so as to form said building material such as a ceramic building material.

In a second aspect the present invention provides a building material characterized in being manufactured by the process according to the invention.

It has surprisingly been found that building materials which have been manufactured by a process where the total amount of raw materials comprises up to 30% w/w digestate on dry weight basis obtained from a Municipal Solid Waste (MSW) process comprising liquefaction of the organic fraction of MSW by addition of one or more enzymes exhibit good properties and provide a sustainable utility for recycling the digestate while saving pristine clay resources.

In one embodiment, the building materials have been manufactured by a process where the total amount of raw materials comprises from 1% w/w to 30% w/w digestate obtained from a Municipal Solid Waste (MSW) process comprising liquefaction of the organic fraction of MSW by addition of one or more enzymes on dry weight basis.

In some embodiments, colouring effects on ceramic building materials, e.g. bricks, can be avoided when using digestate as raw material. The digestate has also surprisingly been found superior to sewage sludge as raw material when manufacturing ceramic building materials at least for providing no discoloration, less shrinkage and/or higher end porosity.

In another embodiment the building material is selected from the group consisting of bricks, light weight aggregates, tiles, floor tiles, roof tiles, wall tiles, drain pipes, sewer pipes, ducts, field drains, clay blocks, and pavers.

In another embodiment the building material is mortar, concrete or cement. In concrete the digestate has been found to be beneficial for serving both as a filler and/or as having pozzolan properties, i.e. increasing strength of the hardened concrete. Furthermore, the digestate did not influence the setting time of the concrete negatively as typically seen for addition of sewage sludge ashes.

It is an object of the present invention to solve the disadvantages of the prior art. In particular it is an object of the invention to recycle waste components by use of digestate as raw material for building materials such as ceramic building materials without introducing severe colouring effects or severe shrinkage effects in said building materials. In a preferred embodiment no severe colouring effects are observed for ceramic building materials such as bricks. Concrete materials comprising digestate ash according to the invention does in some embodiments have a reddish colouring.

DESCRIPTION

Figure 1:
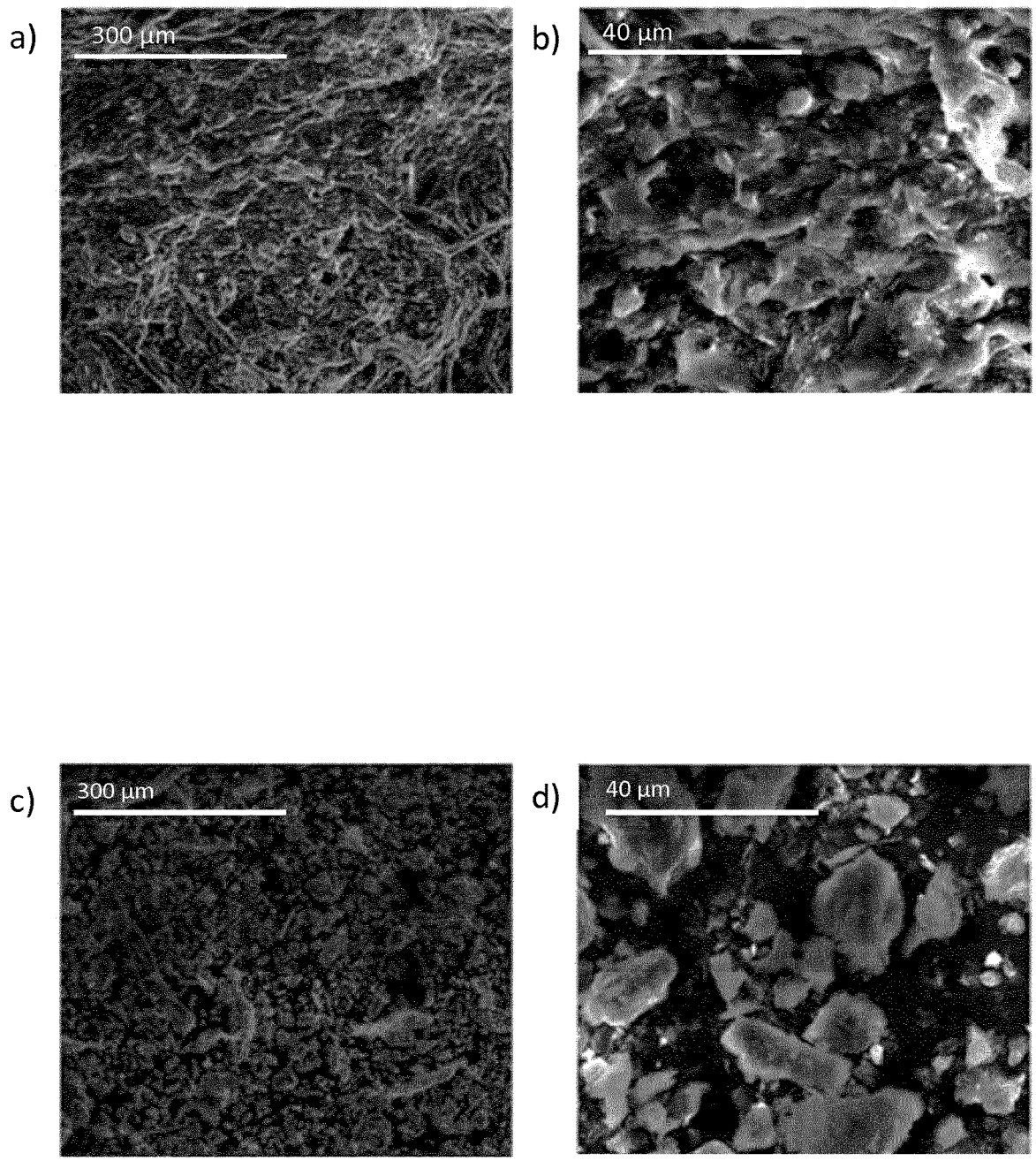
FIG. 1. Scanning electron microscope (SEM) analysis of Solid Digestate (SD) and Dried Digestate (DD); a) SD magnified 200 times, b) SD magnified 1500 times, c) DD magnified 200 times and d) DD magnified 1500 times.

In a first aspect the present invention provides a process for manufacture of a building material such as a ceramic building material comprising the steps of:
  mixing clay and/or sand with digestate from a Municipal Solid Waste (MSW) process comprising liquefaction of the organic fraction of MSW by addition of one or more enzymes,
  optionally adjusting the water contents of the mixture,
  shaping the mixture,
  drying the shaped mixture, and
  optionally firing the shaped mixture,
so as to form said building material such as said ceramic building material.

The adjustment of the water contents of the mixture can be addition of water and/or a water comprising fraction. Alternatively, the adjustment of the water contents can be removal of water such as by evaporation.

Digestate from the MSW Process Comprising Liquefaction of the Organic Fraction of MSW by Addition of One or More Enzymes.

The term "digestate" as used herein is intended to mean the remnant fraction obtained from an anaerobic digestion. The term digestate includes the remnant fraction directly obtained from the anaerobic digestion, but also includes dewatered digestate and dried digestate as well as digestate ash.

The term "digestate from a Municipal Solid Waste (MSW) process comprising liquefaction of the organic fraction of MSW by addition of one or more enzymes" is intended to mean the remnant fraction obtained from anaerobic digestion of the slurry of biodegradable components obtained from a MSW process, where MSW is fermented in a reactor under conditions where microorganisms including lactic acid bacteria and one or more added enzymes are active to liquefy biodegradable materials in the MSW. The term digestate thus includes digestate as obtained directly from the anaerobic digestion and dewatered digestate and dried digestate as well as digestate ash or any combination of these products.

In one embodiment the MSW is sorted MSW, i.e. where non-biodegradable materials such as metal and/or plastic items have been removed. In another more preferred embodiment, the MSW is unsorted and thus enters the reactor for biodegradation and subsequently a separation is done to obtain a slurry of biodegradable components (often termed bioliquid) which is subjected to anaerobic digestion to form biomethane and digestate.

MSW is by nature typically heterogeneous. The MSW fed into the MSW process comprising liquefaction of the organic fraction of MSW by addition of one or more enzymes is a waste fraction which is typically available in cities where it comprises any mixture of cellulosic, plant, animal, plastic, metal and glass waste. MSW thus includes but is not limited to comprise the following:

Garbage collected in normal municipal collections systems, optionally processed in some central sorting, shredding or pulping device such as Dewaster® or reCulture®; solid waste sorted from households, including both organic fractions and paper rich fractions; waste fractions derived from industry such as restaurant industry, food processing industry, general industry; waste fractions from paper industry; waste fractions from recycling facilities; waste fractions from food or feed industry; waste fractions from the medicinal industry; waste fractions derived from agriculture or farming related sectors; waste fractions from processing of sugar or starch rich products; contaminated or in other ways spoiled agriculture products such as grain, potatoes and beets not exploitable for food or feed purposes; garden refuse. At least in the case of household waste, composition exhibits seasonal and geographical variation.

In some embodiments, MSW is processed as "unsorted" wastes. The term "unsorted" as used herein refers to a process in which MSW is not substantially fractionated into separate fractions such that biogenic material is not substantially separated from plastic and/or other non-biogenic material. As used herein the term "biogenic" refers to materials that are bio-degradable and comprise materials derived from living organisms. Waste may be "unsorted" as used herein notwithstanding removal of some large objects or metal objects and notwithstanding some separation of plastic and/or other non-biogenic material. The terms "unsorted waste" (or "unsorted MSW") as used herein refers to waste comprising a mixture of biogenic and non-biogenic material in which 15% by weight or greater of the dry weight is non-biogenic material.

Typically unsorted MSW comprises biogenic wastes, including food and kitchen waste, paper- and/or cardboard-containing materials, food wastes and the like; recyclable materials, including glass, bottles, cans, metals, and certain plastics; other burnable materials, which while not practically recyclable per se may give heat value in the form of refuse derived fuels; as well as inert materials, including ceramics, rocks, and various forms of debris.

In some embodiments, MSW can be processed as "sorted" waste. The term "sorted" as used herein refers to a process in which MSW is substantially fractionated into separate fractions such that biogenic material is substantially separated from plastic and/or other non-biogenic material. The term "sorted waste" (or "sorted MSW") as used herein refers to waste in which less than 15% by weight of the dry weight is non-biogenic material. In some embodiments, MSW can be source-separated organic waste comprising predominantly fruit, vegetable and/or animal wastes. A variety of different sorting systems can be applied to unsorted MSW, including source sorting, where households dispose of different waste materials separately. Alternatively, industrial sorting systems can be used.

In some embodiments, wastes may be lightly sorted yet still produce a waste fraction that is "unsorted" as used herein. In some embodiments, unsorted MSW is used in which greater than 15% by weight of the dry weight is non-biogenic material, or greater than 18%, or greater than 20%, or greater than 21%, or greater than 22%, or greater than 23%, or greater than 24%, or greater than 25%.

In practicing methods of the invention, water content of the MSW is adjusted so that the MSW comprises a non-water content of between 10 and 50% by weight, or in some embodiments between 12 and 40%, or between 13 and 35%, or between 14 and 30%, or between 15 and 25%. In some embodiments the water content is considered to be "adjusted" as used herein where the MSW comprises the appropriate non-water content, whether or not water has been directly added. MSW typically comprises considerable water content. All other solids comprising the MSW are termed "non-water content" as used herein. The level of water content used in practicing methods of the invention relates to several interrelated variables. Methods of the invention typically produce a biogenic slurry. As will be readily understood, the slurry is biogenic where it comprises predominantly biogenic material, but may also include non-biogenic contaminants. A slurry is "liquid" as used herein to the extent that it is pumpable, notwithstanding substantial content of undissolved solids.

As will be readily understood by one skilled in the art, the capacity to render solid components into a liquid slurry is increased with increased water content. Effective pulping of paper and cardboard, which comprise a substantial fraction of MSW in some countries, is typically improved where water content is increased. Water content provides a medium in which the microbial preparation can propagate and which dissolves metabolites. Further, as is well known in the art, enzyme activities can exhibit diminished activity when hydrolysis is conducted under conditions with low water content. For example, cellulases typically exhibit diminished activity in hydrolysis mixtures that have non-water content higher than about 10% by weight. In the case of cellulases, which degrade paper and cardboard, an effectively linear inverse relationship has been reported between substrate concentration and yield from the enzymatic reaction per gram substrate.

In some embodiments, part of the water content should normally be added to the waste in order to achieve an appropriate non-water content.

The person skilled in the art will readily be able to determine an appropriate quantity of water content, if any, to add to wastes in adjusting water content. Typically, as a practical matter, notwithstanding some variability in the composition of MSW being processed, it is convenient to add a relatively constant mass ratio of water (which includes aqueous solution), in some embodiments between 0.8 and 1.8 kg water per kg MSW, or between 0.5 and 2.5 kg water per kg MSW, or between 1.0 and 3.0 kg water per kg MSW. As a result, the actual non-water content of the MSW during processing may vary within the appropriate range.

A variety of different microbial fermentation reactors may be used. In some embodiments, a reactor similar to that described in WO2011/032557 can be used. WO2011/032557 is hereby incorporated-by-reference in its entirety in the present patent application.

Agitation may be achieved by a variety of different means. Agitation is advantageous because it promotes not only microbial fermentation per se but also hydrolysis catalysed by one or more enzymes that are added and additionally provided by the living microorganisms.

In order for optimal microbial and enzymatic activity in the reactor temperatures are between 35 degrees C. and 75 degrees C., such as between 40 degrees C. and 55 degrees C., or between 45 degrees C. and 50 degrees C. In one embodiment, the MSW degradation process is conducted at temperatures of less than 75 degrees C., such as less than 55 degrees C. In one embodiment, the pH during the MSW degradation process is between 4.2 and 6.0. In one embodiment, the residence time in the reactor for MSW degradation is between 1 and 72 hours, such as between 5 and 50 hours, such as between 10 and 20 hours, such as between 12 and 18 hours.

A variety of different means may be used to achieve and maintain a lactic acid bacteria concentration of at least 1

$0.0 \times 10^{10}$ CFU (colony forming unit)/L during the course of fermentation. As used herein the lactic acid bacteria concentration is maintained at a concentration during the fermentation step prior to separation of non-degradable solids, to the extent that the concentration of live bacterial cells in the fermentation is on average at least 1 $0.0 \times 10^{10}$ CFU/L over the course of the fermentation. An average of at least 1 $0.0 \times 10^{10}$ CFU/L during the fermentation is typically demonstrated by a series of measurements on samples taken before and after or during the fermentation. The measurement of CFU/L is determined by a measurement expressed as CFU per g total solids present in a representative sample of the mixture, and then expressed as a measurement per L by a measurement of weight percentage total solids content of the mixture In some embodiments, microbially-derived cellulase activity may be provided by specialized cellulase-secreting organisms, which have been included in an inoculum applied to the incoming MSW stream. In some embodiments, microbially-derived cellulase activity may reach levels of at last 50 FPU/L, or at least 75 FPU/L, or at least 100 FPU/L, or at least 300 FPU/L, or at least 500 FPU/L, or at least 700 FPU/L, or at least 1000 FPU/L. In some embodiments, it can be advantageous to add isolated enzyme preparations to the microbial fermentation mixture, including amylase preparations and/or mannanase preparations, or other enzyme preparations.

The duration of microbial fermentation prior to separation of non-degradable solids and bio-degradable slurry is determined by the average residence time within the microbial fermentation reactor. In some embodiments, average residence time of the MSW stream in microbial fermentation prior to separation of degradable materials is 18 hours or less, or 24 hours or less, or 36 hours or less, or 48 hours or less, or 72 hours or less or between 10 hours and 24 hours, or between 24 hours and 36 hours or between 36 hours and 48 hours, or between 48 hours and 60 hours, or between 60 hours and 72 hours, or any combination of these intervals.

A stream of unsorted MSW is preferably continuously introduced to the reactor and a stream of partially hydrolysed, fermented MSW is preferably continuously removed from the reactor. In some embodiments, however, the stream of MSW may be introduced in a pulsatile manner, with one injection of MSW, followed by a pause, followed by a subsequent injection of MSW. Similarly in some embodiments the stream of partially hydrolysed, fermented MSW may be removed from the reactor in a pulsatile manner, with one ejection of MSW, followed by a pause, followed by a subsequent ejection of MSW and so on.

After removal from the microbial fermentation reactor, the partially hydrolysed, fermented MSW is subject to a separation step whereby non-degradable solids are removed to provide a slurry of biodegradable components. This separation step, and subsequent processing, can be achieved in a variety of different ways.

In some embodiments, the separation step is achieved in two steps. First, a ballistic separator removes two streams of non-degradable materials, producing a "two dimensional" (2D) fraction comprising plastic bags and other generally formless material, a "three dimensional" (3D) fraction comprising bottles and containers having a definite shape, and a volume of a biogenic liquid slurry of bio-degradable components (termed bioliquid). In a second step, the 2D fraction is further subject to pressing with a screw press or similar device to further increase the yield of the biogenic slurry. In some embodiments, the 2D fraction is further subject to washing, in order to further recover bio-degradable material.

The wash waters obtained in this step can then be maintained at the fermentation temperature and used to wet and also inoculate incoming unsorted MSW. Unsorted MSW is subject to a biological sorting process that produces four products—a biogenic slurry suitable for production of biomethane and digestate, inerts (glass and sand) for recycling, and both a "two dimensional" (2D) and a "three dimensional" (3D) fraction of inorganic materials suitable for RDF production as well as for recycling of metals, plastic and wood. MSW from urban areas is collected as-is in plastic bags. The MSW is transported to the plant where it is typically stored in a silo until processing. Depending on the character of the MSW a sorting step can be installed in front of the reactor to take out oversize particles (e.g. above 500 mm). A stream of unsorted MSW is heated and its non-water content adjusted by addition of heated aqueous solution. In some embodiments, cellulase activity provided by isolated enzyme preparations may be added to facilitate rapid degradation of the biodegradable component of the MSW. In some embodiments isolated enzyme preparations are added to the heated MSW at an appropriate non-water content. In some embodiments, no isolated enzyme preparations are added and microbial hydrolysis and fermentation is provided by maintaining lactic acid bacteria during the course of fermentation at levels of live bacterial cells at least 1 $0.0 \times 10^{10}$ CFU/L. The MSW with added one or more enzymes, can be incubated in a microbial fermentation reactor similar to that described in WO2011/032557. While continuously introducing MSW into the reactor and continuously removing partially degraded MSW from the reactor, a certain average residence time is obtained. Partially degraded MSW removed from the reactor can subsequently be subject to two distinct separation steps. First, a ballistic separator, often used in sorting, can be used, for example having sieves between 20-50 mm to produce a biogenic slurry stream, as well as a 3D non-degradable fraction and a 2D non-degradable fraction.

In some embodiments, microbial fermentation is accomplished concurrently with enzymatic hydrolysis. Enzymatic hydrolysis can be achieved using a variety of different means. In some embodiments, enzymatic hydrolysis can be achieved using isolated enzyme preparations. As used herein, the term "isolated enzyme preparation" refers to a preparation comprising enzyme activities that have been extracted, secreted or otherwise obtained from a biological source and optionally partially or extensively purified. A variety of different enzyme activities may be advantageously used to practice methods of the invention. Considering, for example, a composition of MSW where paper comprises the greatest single component, by dry weight, of the biogenic material it will be readily apparent to the person skilled in the art, for typical household waste, cellulose-degrading activity will be particularly advantageous. In paper-containing wastes, cellulose has been previously processed and separated from its natural occurrence as a component of lignocellulosic biomass, intermingled with lignin and hemicellulose. Accordingly, paper-containing wastes can be advantageously degraded using a comparatively "simple" cellulase preparation.

"Cellulase activity" refers to enzymatic hydrolysis of 1,4-B-D-glycosidic linkages in cellulose. In isolated cellulase enzyme preparations obtained from bacterial, fungal or other sources, cellulase activity typically comprises a mixture of different enzyme activities, including endoglucanases and exoglucanases (also termed cellobiohydrolases), which respectively catalyse endo- and exo-hydrolysis of 1,4-$\alpha$-D-glycosidic linkages, along with B-glucosidases, which hydrolyse the oligosaccharide products of exoglucanase hydrolysis to monosaccharides. Complete hydrolysis of insoluble cellulose typically requires a synergistic action between the different activities.

As a practical matter, it can be advantageous in some embodiments to simply use a commercially available isolated cellulase preparation optimized for lignocellulosic biomass conversion, since these are readily available at comparatively low cost.

The term "optimized for lignocellulosic biomass conversion" refers to a product development process in which enzyme mixtures have been selected and modified for the specific purpose of improving hydrolysis yields and/or reducing enzyme consumption in hydrolysis of pretreated lignocellulosic biomass to fermentable sugars.

However, commercial cellulase mixtures optimized for hydrolysis of lignocellulosic biomass typically contain high levels of additional and specialized enzyme activities.

Simpler isolated cellulase preparations may also be effectively used to practice methods of the invention. Suitable cellulase preparations may be obtained by methods well known in the art from a variety of microorganisms, including aerobic and anaerobic bacteria, white rot fungi, soft rot fungi and anaerobic fungi.

In addition to cellulase activity, some additional enzyme activities which can prove advantageous in practicing methods of the invention include enzymes which act upon food wastes, such as proteases, glucoamylases, endoamylases, proteases, pectin esterases, pectin lyases, and lipases, and enzymes which act upon garden wastes, such as xylanases, and xylosidases. In some embodiments it can be advantageous to include other enzyme activities such as laminarases, ketatinases and/or laccases.

Enzymatic hydrolysis using cellulase activity will typically sacchartify cellulosic material. Accordingly, during enzymatic hydrolysis, solid wastes are both saccharified and liquefied, that is, converted from a solid form into a liquid slurry.

In some embodiments, MSW can be inoculated with naturally occurring bacteria, by continued recycling of wash waters or process solutions used to recover residual organic material from non-degradable solids.

In some embodiments, the digestate is produced by processing municipal solid waste (MSW) by a method comprising the steps of
  (i). providing MSW with added one or more enzymes at a non-water content of between 5 and 40% and at a temperature within the range of 35 and 75 degrees C.,
  (ii). subjecting the biodegradable parts of the MSW to microbial fermentation and enzymatic hydrolysis at a temperature within the range of 35 and 75 degrees C. resulting in partial liquefaction of biodegradable parts of the waste and accumulation of microbial metabolites, followed by
  (iii). sorting of the liquefied, biodegradable parts of the waste from non-biodegradable solids to produce a bio-degradable slurry characterized in comprising dissolved volatile solids of which at least 25% by weight comprise any combination of acetate, butyrate, ethanol, formate, lactate and/or propionate, followed by
  (iv). anaerobic digestion of the bioliquid to produce biomethane and digestate.

The preceding detailed discussion concerning embodiments of methods of degrading MSW including details concerning compositional features of the biodegradable slurry obtained, may be applied to provide biomethane and digestate. In some embodiments, any of the details concerning compositional features of bio-degradable slurry may be obtained by a process in which unsorted MSW subject to microbial fermentation is subject to separation of non-degradable solids to produce a bio-degradable slurry, which slurry is then subject to continued fermentation at a temperature within the range of 35 to 75 degrees C., or between 40 and 55 degrees C., or between 45 and 50 degrees C., at a pH within the range 4.2 to 6.0 for a time of between 1 and 72 hours. In some embodiments, this continued fermentation is supplemented in that bio-degradable material recovered by sieves or other systems such that the material was not technically part of the initially recovered bio-degradable slurry, can be added to the slurry.

The metabolic dynamics of microbial communities engaged in anaerobic digestion are complex. In typical anaerobic digestion (AD) for production of methane biogas, biological processes mediated by microorganisms achieve four primary steps—hydrolysis of biological macromolecules into constituent monomers or other metabolites; acidogenesis, whereby short chain hydrocarbon acids and alcohols are produced; acetogenesis, whereby available nutrients are catabolized to acetic acid, hydrogen and carbon dioxide; and methanogenesis, whereby acetic acid and hydrogen are catabolized by specialized archaea to methane and carbon dioxide. The hydrolysis step is typically rate-limiting. Accordingly, it is advantageous in preparing substrates for biomethane production that these be previously hydrolysed through some form of pretreatment. In some embodiments, methods of the invention combine microbial fermentation with enzymatic hydrolysis of MSW as both a rapid biological pretreatment for eventual biomethane production as well as a method of sorting degradable organic components from otherwise unsorted MSW.

In contrast to other methods the MSW degradation process described herein typically produce liquid biomethane substrates comprising at least 40% dissolved volatile solids.

Two-stage anaerobic digestion systems have also been reported in which the first stage process hydrolyses biomethane substrates include source-sorted organic components of MSW and other specialized biogenic substrates. During the first anaerobic stage, which is typically thermophillic, higher chain polymers are degraded, and volatile fatty acids produced. This is followed by a second-stage anaerobic stage conducted in a physically separate reactor in which methanogenesis and acetogenesis dominate. Reported two-stage anaerobic digestion systems have typically utilized source-sorted, specialized biogenic substrates having less than 7% total solids, even though some newer two-stage AD systems have been reported which utilize source-sorted, specialized biogenic substrates at levels as high as 10% total solids. Certainly, none of the reported two-stage anaerobic digestion systems have ever contemplated use of unsorted MSW as a substrate, much less in order to produce a high solids liquid biomethane substrate. Two stage anaerobic digestion seeks to convert solid substrates, continuously feeding additional solids to and continuously removing volatile fatty acids from the first stage reactor.

In some embodiments, the method of producing biomethane and digestate comprises the steps of
  (i). providing a liquid biomethane substrate pre-conditioned by microbial fermentation such that at least 40% by weight of the non-water content exists as dissolved volatile solids, which dissolved volatile solids comprise at least 25% by weight of any combination of acetate, butyrate, ethanol, formate, lactate and/or propionate,
  (ii). transferring the liquid substrate into an anaerobic digestion system, followed by (iii). conducting anaerobic digestion of the liquid substrate to produce biomethane and digestate.

In some embodiments, the MSW degradation process provides a liquid biomethane substrate produced by microbial fermentation and hydrolysis by one or more added enzymes of municipal solid waste (MSVV), alternatively, comprising adding one or more enzymes for enzymatically hydrolysing and microbially fermenting MSW characterized in that
at least 40% by weight of the non-water content exists as dissolved volatile solids, which dissolved volatile solids comprise at least 25% by weight of any combination of acetate, butyrate, ethanol, formate, lactate and/or propionate.

In some embodiments, the MSW degradation process provides an organic liquid biogas substrate produced by microbial fermentation and enzymatic hydrolysis of municipal solid waste (MSVV) characterized in that
at least 40% by weight of the non-water content exists as dissolved volatile solids, which dissolved volatile solids comprise at least 25% by weight of any combination of acetate, butyrate, ethanol, formate, lactate and/or propionate.

In some embodiments, the MSW degradation process provides a method of producing biogas and digestate comprising the steps of
(i). providing a liquid biogas substrate pre-conditioned by microbial fermentation such that at least 40% by weight of the non-water content exists as dissolved volatile solids, which dissolved volatile solids comprise at least 25% by weight of any combination of acetate, butyrate, ethanol, formate, lactate and/or propionate,
(ii). transferring the liquid substrate into an anaerobic digestion system, followed by
(iii). conducting anaerobic digestion of the liquid substrate to produce biomethane and digestate.

As used herein the term "anaerobic digestion system" refers to a fermentation system comprising one or more reactors operated under controlled aeration conditions in which methane gas is produced in each of the reactors comprising the system. Methane gas is produced to the extent that the concentration of metabolically generated dissolved methane in the aqueous phase of the fermentation mixture within the "anaerobic digestion system" is saturating at the conditions used and methane gas is emitted from the system.

In some embodiments, the "anaerobic digestion system" is a fixed filter system. A "fixed filter anaerobic digestion system" refers to a system in which an anaerobic digestion consortium is immobilized, optionally within a biofilm, on a physical support matrix.

In one embodiment, the "anaerobic digestion system" is a reactor comprising an insert comprising a biofilm such as a methane-producing biofilm immobilized on a carrier matrix as described in WO 2016/050893. In a specific embodiment the "anaerobic digestion system" comprises an insert comprising one or more baffles defining at least two open compartments, said one or more baffles comprising one or more open edges, thereby when inserted into a tank reactor and when said tank reactor is in operation said one or more open edges define an underflow or an overflow aperture thus forcing a fluid to flow upwardly or downwardly across said underflow or said overflow aperture.

In another embodiment, the "anaerobic digestion system" is a reactor comprising an insert comprising a biofilm such as a methane-producing biofilm immobilized on a carrier matrix as described in WO 2017/174093. In a specific embodiment the "anaerobic digestion system" comprises an insert, said insert comprising an outer tubular structure having a longitudinal extension, being made from a fluidic non-penetrable material and having an opening at each end of the outer tubular structure so as defining an open compartment forming a flow passage inside the outer tubular structure extending between said openings, and one or more fluid penetrable biofilm carriers arranged inside said outer tubular structure, so that when the insert is arranged in a tank reactor and when said tank reactor is in operation, the plug flow direction of the fluid inside the insert is in the longitudinal direction of the insert.

WO 2016/050893 and WO 2017/174093 are hereby incorporated-by-reference in their entirety in the present patent application.

In some embodiments, the liquid biomethane substrate comprises at least 8% by weight total solids, or at least 9% total solids, or at least 10% total solids, or at least 11% total solids, or at least 12% total solids, or at least 13% total solids. "Total solids" as used herein refers to both soluble and insoluble solids, and effectively means "non-water content." Total solids are measured by drying at 60 degrees C. until constant weight is achieved.

In some embodiments, microbial fermentation of MSW is conducted under conditions that discourage methane production by methanogens, for example, at pH of 6.0 or lower, or at pH less than 5.8, or at pH less than 5.6, or at pH less than 5.5. In some embodiments, the liquid biomethane substrate comprises less than saturating concentrations of dissolved methane. In some embodiments, the liquid biomethane substrate comprises less than 15 mg/L dissolved methane, or less than 10 mg/L, or less than 5 mg/L. In some embodiments, prior to anaerobic digestion to produce biomethane and digestate, one or more components of the dissolved volatile solids may be removed from the liquid biomethane substrate by distillation, filtration, electrodialysis, specific binding, precipitation or other means well known in the art. In some embodiments, ethanol or lactate may be removed from the liquid biomethane substrate prior to anaerobic digestion to produce biomethane and digestate.

In some embodiments, a solid substrate such as MSW or fiber fraction from pretreated lignocellulosic biomass, is subject to enzymatic hydrolysis by one or more added enzymes concurrently with microbial fermentation so as to produce a liquid biomethane substrate pre-conditioned by microbial fermentation such that at least 40% by weight of the non-water content exists as dissolved volatile solids, which dissolved volatile solids comprise at least 25% by weight of any combination of acetate, butyrate, ethanol, formate, lactate and/or propionate. In some embodiments, a liquid biomethane substrate having the above-mentioned properties is produced by concurrent enzymatic hydrolysis and microbial fermentation of liquefied organic material obtained from unsorted MSW by an autoclave process. In some embodiments, pretreated lignocellulosic biomass can be mixed with enzymatically hydrolysed and microbially fermented MSW which has been added one or more enzymes, optionally in such manner that enzymatic activity from the MSW-derived bioliquid provides enzymatic activity for hydrolysis of the lignocellulosic substrate to produce a composite liquid biomethane substrate derived from both MSW and pretreated lignocellulosic biomass.

Building Materials.

Building materials such as bricks, tiles and lightweight aggregates (LWAs) are made from mainly clay and/or sand by a process where the raw materials and optionally water are mixed to a proper consistency allowing the shaping of the article which is to be made into the building material. Following a period of drying the shaped articles are preferably fired (or burned) in a process of increasing temperature until the desired building material is formed and can be cooled.

In one embodiment, the building material is selected from the group consisting of bricks, light weight aggregates, tiles, floor tiles, roof tiles, wall tiles, drain pipes, sewer pipes, ducts, field drains, clay blocks, and pavers. In another embodiment, the building material is a concrete additive, concrete, cement and/or mortar comprising digestate.

The digestate from a Municipal Solid Waste (MSW) process comprising liquefaction of the organic fraction of MSW by addition of one or more enzymes (digestate) may be added to the clay prior to mixing either as digestate obtained directly from the anaerobic digestion of the MSW process, i.e. high water contents (termed Raw Digestate and abbreviated RD), or as a dewatered digestate (abbreviated SD for Solid Digestate) obtained from the same process or may be dried as Dried Digestate (abbreviated DD). The digestate may even be digestate ash (abbreviated DA) where water and organic matter has been eliminated or a mixture of directly obtained digestate, dewatered digestate, dried digestate and/or digestate ash. Preferably, dewatered digestate is used in the process for manufacture of a building material such as a ceramic building material. Dewatered digestate provides a suitable amount of water when mixed with clay to form ceramic articles. Further, it has surprisingly been found that digestate which has not been dried exhibit better properties similar to clay, and not dried digestate results in particle size distribution (smaller particles) which may improve brick density and strength.

In one embodiment, the digestate has a moisture content of at least 10% w/w, at least 15% w/w, at least 20% w/w, at least 25% w/w, or at least 30% w/w. In another embodiment, the digestate has a moisture content in the range from about 55% w/w to about 85% w/w or from about 65% w/w to about 75% w/w. In another embodiment the digestate has a content of organic matter in the range from about 45% w/w to about 75% w/w on dry weight basis, or in the range from about 50% w/w to about 70% w/w on dry weight basis, or about 60% w/w on dry weight basis. In yet another embodiment the digestate has a content of inorganic matter in the range from about 25% w/w to about 55% w/w on dry weight basis, or in the range from about 30% w/w to about 50% w/w on dry weight basis, or about 40% w/w on dry weight basis.

Whereas sewage sludge generally may not be suitable as an additive to concrete, digestate can be used as a concrete additive. Without wishing to be bound by theory this difference may be linked to the lower phosphor contents in the digestate as compared to sewage sludge. The lower phosphor contents typically result in unaffected setting time of the concrete. Also, digestate ash (DA) has been found to exhibit pozzolan properties in concrete which may be provided by siliceous and aluminous materials which, in itself, possesses little or no cementitious value but which will, in finely divided form in the presence of moisture, react chemically with calcium hydroxide at ordinary temperature to form compounds possessing cementitious properties.

In another embodiment, the digestate ash has been obtained by mono incineration and/or other thermal process such as pyrolysis or gasification.

In yet another embodiment, a process for manufacturing cement and concrete based building materials comprises the steps of conventional cement production typically comprising the following steps:

Mixing and finely grinding raw materials such as limestone, clay, shale, and/or sand.

Firing at temperatures up to around 1500 degrees C.,

Optionally firing digestate partly as fuel input and partly as raw material substitution, as non-combustible fraction becomes incorporated in cement clinker product, cement clinker cooling, grinding and adding gypsum and potentially other additives, such as digestate.

In another aspect, the present invention provides a method for concrete processing comprising the steps of:

mixing the main components cement, water, sand and stones and potentially other additives such as digestate shaping the mixture drying and setting (solidification and hardening of the cement binder phase).

The term "about" as used herein in relation to a number means plus or minus 5%. Hence, "about 25% w/w" means from 23.75% w/w to 26.25%.

Ceramic building materials, e.g. bricks, made from a total of raw materials with up to 30% w/w dry basis digestate typically shows no sign of discoloration and the mineral structure in the bricks or lightweight aggregates typically remain unchanged as compared to not adding digestate. The brick furthermore has an acceptable content of heavy metals, and the leaching of heavy metals is also acceptable (Cu, Zn, Pb, Cd) when compared to found levels of heavy metals in commercial bricks (Karius, V. et al., pH and grain-size variation in leaching tests with bricks made of harbour sediments compared to commercial bricks. *Science of the Total Environment*, 278(1-3), pp. 73-85).

In one embodiment, the building material is manufactured from a total amount of raw materials comprising from 1% w/w to 30% w/w digestate on dry weight basis, or from 5% w/w to 30% w/w digestate on dry weight basis, or from 10% w/w to 30% w/w digestate on dry weight basis. The building material is preferably manufactured from a total amount of raw materials comprising from 1% w/w to 30% w/w digestate on dry weight basis such as from 1% w/w to 2% w/w digestate on dry weight basis, from 1% w/w to 5% w/w digestate on dry weight basis, from 1% w/w to 10% w/w digestate on dry weight basis, from 10% w/w to 15% w/w. digestate on dry weight basis, from 15% w/w to 30% w/w digestate on dry weight basis, from 20% w/w to 30% w/w digestate on dry weight basis, for example from 2% w/w to 4% w/w digestate on dry weight basis, such as from 4% w/w to 6% w/w digestate on dry weight basis, for example from 6% w/w to 8% w/w digestate on dry weight basis, such as from 8% w/w to 10% w/w digestate on dry weight basis, for example from 10% w/w to 12% w/w digestate on dry weight basis, such as from 12% w/w to 14% w/w digestate on dry weight basis, for example from 14% w/w to 16% w/w digestate on dry weight basis, such as from 16% w/w to 18% w/w digestate on dry weight basis, for example from 18% w/w to 20% w/w digestate on dry weight basis, such as from 20% w/w to 22% w/w digestate on dry weight basis, for example from 22% w/w to 24% w/w digestate on dry weight basis, such as from 24% w/w to 26% w/w digestate on dry weight basis, for example from 26% w/w to 28% w/w digestate on dry weight basis, such as from 28% w/w to 30% w/w digestate on dry weight basis, or any combination of these intervals.

In another embodiment, the building material is manufactured from a total amount of raw materials comprising at least 1% w/w digestate ash on dry weight basis, at least 10% w/w digestate ash on dry weight basis, at least 20% w/w digestate ash on dry weight basis, at least 50% w/w digestate ash on dry weight basis, at least 75% w/w digestate ash on dry weight basis, or at least 90% w/w digestate ash on dry weight basis.

The firing temperature typically increases gradually, e.g. by 5 degrees C. per minute, until the final firing temperature is attained. The firing temperature may be in the range from about 900 degrees C. to about 1200 degrees C. In one embodiment, the firing temperature is from about 1000 degrees C. to about 1100 degrees C. The strength of a ceramic building material such as a brick which comprises digestate as a raw material can be enhanced by optimizing the firing process (temperature and/or time).

Preferably, not dried digestate and a relatively high firing temperature is used, since this may also reduce the water absorption of the building material and thereby improve weather resistance.

For lightweight aggregates the present invention of using digestate as raw material has the advantage of resulting in an increased porosity of the material and reducing and/or eliminating the shrinkage which is observed when using sewage sludge as raw material. When using digestate as raw material for lightweight aggregates shrinking is less than the shrinking observed for sewage sludge. Under preferred conditions the lightweight aggregate shrinking is not impaired when digestate is used as raw material. The overall advantage of manufacturing building materials comprising digestate is to provide a sustainable solution for recycling the waste derived digestate from the MSW process comprising liquefaction of the organic fraction of MSW by addition of one or more enzymes, where potential micro and macroplastic and organic contaminants (xenobiotics) are destroyed effectively and heavy metals are stabilised in the building material structure and conserving pristine raw material resources.

The following listed embodiments of the invention are not to be construed as limiting the invention:

1. A process for manufacture of a building material such as a ceramic building material comprising the steps of:
    mixing clay and/or sand with digestate obtained from a Municipal Solid Waste (MSW) process comprising liquefaction of the organic fraction of MSW by addition of one or more enzymes,
    optionally adjusting the water contents of the mixture,
    shaping the mixture,
    drying the shaped mixture, and
    optionally firing the shaped mixture,
so as to form said building material.

2. The process according to embodiment 1 comprising the steps of:
    mixing clay with digestate obtained from a Municipal Solid Waste (MSW) process comprising liquefaction of the organic fraction of MSW by addition of one or more enzymes,
    optionally adjusting the water contents of the mixture,
    shaping the mixture,
    drying the shaped mixture, and
    optionally firing the shaped mixture,
so as to form said building material.

3. The process according to any of the preceding embodiments, wherein said digestate is selected from the group consisting of digestate directly obtained by said MSW process, dewatered digestate, dried digestate and digestate ash.

4. The process according to any of the preceding embodiments, wherein said digestate is dried digestate or digestate ash.

5. The process according to embodiment 4, wherein said dried digestate or digestate ash is pulverized, such as by milling.

6. The process according to any of the preceding embodiments, wherein said building material is bricks.

7. The process according to any one of embodiments 1-5, wherein said building material is lightweight aggregates.

8. The process according to any of embodiments 1-5, wherein said building material is selected from the group consisting of bricks, light weight aggregates, tiles, floor tiles, roof tiles, wall tiles, drain pipes, sewer pipes, ducts, field drains, clay blocks, and pavers.

9. The process according to any of embodiments 1-5, wherein said building material is cement, concrete or mortar.

10. The process according to any of the preceding embodiments, wherein said digestate is obtained from MSW which has been degraded by microbial and enzymatic treatment to obtain a bioliquid which has been subjected to anaerobic digestion.

11. The process according to any of the preceding embodiments, wherein said digestate has a moisture content of at least 10% w/w, at least 15% w/w, at least 20% w/w, at least 25% w/w or at least 30% w/w.

12. The process according to any of the preceding embodiments, wherein said digestate has a moisture content in the range from about 50% w/w to about 90% w/w, from about 55% w/w to about 85% w/w, from about 50% w/w to about 70% w/w, from about 70% w/w to about 90% w/w, from about 65% w/w to about 75% w/w, from 65% w/w to 75% w/w or about 70% w/w.

13. The process according to any of the preceding embodiments, wherein said digestate has a content of organic matter in the range from about 45% w/w to about 75% w/w on dry weight basis, from about 45% w/w to about 60% w/w on dry weight basis, or from about 50% w/w to about 70% w/w on dry weight basis, from about 60% w/w to about 75% w/w on dry weight basis, from 55% w/w to 65% w/w on dry weight basis, or from about 60% w/w on dry weight basis.

14. The process according to any of the preceding embodiments, wherein said digestate has a content of inorganic matter in the range from about 25% w/w to about 55% w/w on dry weight basis, in the range from about 25% w/w to about 45% w/w on dry weight basis, in the range from about 25% w/w to about 35% w/w on dry weight basis, in the range from about 35% w/w to about 55% w/w on dry weight basis, in the range from about 45% w/w to about 55% w/w on dry weight basis, in the range from about 35% w/w to about 45% w/w on dry weight basis, in the range from about 30% w/w to about 50% w/w on dry weight basis, or about 40% w/w on dry weight basis.

15. The process according to any of the preceding embodiments, wherein said digestate has a content of phosphor (P) in the digestate ash which is less than about 2% w/w, less than about 1.5% w/w, less than about 1.0% w/w, less than about 0.5% w/w, less than about 0.4% w/w, less than about 0.3% w/w, less than about 0.25% w/w or less than about 0.20% w/w.

16. The process according to any of the preceding embodiments, wherein said digestate has a content of iron (Fe) in the digestate ash which is less than about 8% w/w, less than about 6% w/w, less than about 5% w/w, less than about 4% w/w, less than about 3% w/w, less than about 2% w/w, less than about 1% w/w, less than about 0.75% or less than about 0.5% w/w.

17. The process according to any of the preceding embodiments, wherein the total amount of raw materials comprises from 1% w/w to 30% w/w digestate on dry weight basis, or from 5% w/w to 30% w/w digestate on dry weight basis, or from 10% w/w to 30% w/w digestate on dry weight basis.
18. The process according to any of the preceding embodiments, wherein the total amount of raw materials comprises from 1% w/w to 30% w/w digestate on dry weight basis, from 1% w/w to 2% w/w digestate on dry weight basis, from 1% w/w to 5% w/w digestate on dry weight basis, from 1% w/w to 10% w/w digestate on dry weight basis, from 10% w/w to 15% w/w. digestate on dry weight basis, from 15% w/w to 30% w/w digestate on dry weight basis, from 20% w/w to 30% w/w digestate on dry weight basis, from 2% w/w to 4% w/w digestate on dry weight basis, from 4% w/w to 6% w/w digestate on dry weight basis, from 6% w/w to 8% w/w digestate on dry weight basis, from 8% w/w to 10% w/w digestate on dry weight basis, from 10% w/w to 12% w/w digestate on dry weight basis, from 12% w/w to 14% w/w digestate on dry weight basis, from 14% w/w to 16% w/w digestate on dry weight basis, from 16% w/w to 18% w/w digestate on dry weight basis, from 18% w/w to 20% w/w digestate on dry weight basis, from 20% w/w to 22% w/w digestate on dry weight basis, from 22% w/w to 24% w/w digestate on dry weight basis, from 24% w/w to 26% w/w digestate on dry weight basis, from 26% w/w to 28% w/w digestate on dry weight basis, from 28% w/w to 30% w/w digestate on dry weight basis, or any combination of these intervals.
19. The process according to any of the preceding embodiments, wherein the total amount of raw materials comprises at least 1% w/w digestate ash on dry weight basis, at least 10% w/w digestate ash on dry weight basis, at least 20% w/w digestate ash on dry weight basis, at least 50% w/w digestate ash on dry weight basis, at least 75% w/w digestate ash on dry weight basis, or at least 90% w/w digestate ash on dry weight basis.
20. The process according to any of embodiments 3-19, wherein said digestate ash has been obtained by mono incineration or other thermal process such as pyrolysis or gasification.
21. The process according to any of the preceding embodiments, wherein the firing temperature is from about 900 degrees C. to about 1200 degrees C.
22. The process according to any of the preceding embodiments, wherein the firing temperature is from about 1000 degrees C. to about 1100 degrees C.
23. The process according to any of the preceding embodiments, wherein said building material is lightweight aggregates and wherein the firing temperature is between 1100 degrees C. and 1200 degrees C.
24. A building material characterized in being manufactured by the process according to any of the preceding embodiments.
25. The building material according to embodiment 24 which has been manufactured by a process where the total amount of raw materials comprises from 1% w/w to 30% w/w digestate on dry weight basis, or from 5% w/w to 30% w/w digestate on dry weight basis, or from 10% w/w to 30% w/w digestate on dry weight basis.
26. The building material according to embodiment 25 which has been manufactured by a process where the total amount of raw materials comprises from 1% w/w to 30% w/w digestate on dry weight basis, from 1% w/w to 2% w/w digestate on dry weight basis, from 1% w/w to 5% w/w digestate on dry weight basis, from 1% w/w to 10% w/w digestate on dry weight basis, from 10% w/w to 15% w/w. digestate on dry weight basis, from 15% w/w to 30% w/w digestate on dry weight basis, from 20% w/w to 30% w/w digestate on dry weight basis, from 2% w/w to 4% w/w digestate on dry weight basis, from 4% w/w to 6% w/w digestate on dry weight basis, from 6% w/w to 8% w/w digestate on dry weight basis, from 8% w/w to 10% w/w digestate on dry weight basis, from 10% w/w to 12% w/w digestate on dry weight basis, from 12% w/w to 14% w/w digestate on dry weight basis, from 14% w/w to 16% w/w digestate on dry weight basis, from 16% w/w to 18% w/w digestate on dry weight basis, from 18% w/w to 20% w/w digestate on dry weight basis, from 20% w/w to 22% w/w digestate on dry weight basis, from 22% w/w to 24% w/w digestate on dry weight basis, from 24% w/w to 26% w/w digestate on dry weight basis, from 26% w/w to 28% w/w digestate on dry weight basis, from 28% w/w to 30% w/w digestate on dry weight basis, or any combination of these intervals.
27. The building material according to any of embodiments 24-26, which has been manufactured from a total amount of raw materials comprising at least 1% w/w digestate ash on dry weight basis, at least 10% w/w digestate ash on dry weight basis, at least 20% w/w digestate ash on dry weight basis, at least 50% w/w digestate ash on dry weight basis, at least 75% w/w digestate ash on dry weight basis, or at least 90% w/w digestate ash on dry weight basis.
28. The building material according to any of embodiments 24-27, wherein the building material is selected from the group consisting of bricks, light weight aggregates, tiles, floor tiles, roof tiles, wall tiles, drain pipes, sewer pipes, ducts, field drains, clay blocks, and pavers.
29. A brick characterized in being manufactured by the process according to any of embodiments 1-23.
30. A light weight aggregate characterized in being manufactured by a process according to any of embodiments 1-23.
31. A material selected from concrete, a concrete additive, cement or mortar characterized in being manufactured from digestate obtained from a Municipal Solid Waste (MSVV) process comprising liquefaction of the organic fraction of MSW by addition of one or more enzymes.
32. A concrete material or a concrete additive characterized in being manufactured from digestate ash obtained from a Municipal Solid Waste (MSW) process comprising liquefaction of the organic fraction of MSW by addition of one or more enzymes.
33. Cement characterized in being manufactured by a process comprising firing, and where said cement is manufactured from digestate obtained from a Municipal Solid Waste (MSVV) process comprising liquefaction of the organic fraction of MSW by addition of one or more enzymes.

EXAMPLES

Example 1. Preparation of Digestate (Raw Digestate, Dewatered Digestate, Dried Digestate, and Digestate Ash)

Digestate for laboratory scale ceramic material experiments was prepared from unsorted European municipal solid waste (MSVV) treated in a demonstration scale Renescience process comprising enzymatic treatment from e.g. one or more added enzymes and subsequently subjected to anaerobic digestion as described in WO2014/198274 and WO2013/18778.

Experiments were conducted at the Renescience demonstration plant at Amager resource center (ARC), Copenhagen, Denmark. The concept of the ARC Renescience Waste Refinery was to sort MSW into four products: A biogenic slurry (in the following called bioliquid) suitable for biomethane production or other processes, inerts (glass and sand) for recycling and both a "two dimensional" (2D) and a "three dimensional" (3D) fraction of inorganic materials suitable for Refuse Derived Fuel (RDF) and Solid Recovered Fuel (SRF) production as well as for recycling of metals, plastic and wood.

MSW from urban areas was collected as-is in plastic bags. The MSW was transported to the Renescience Waste Refinery where it was stored in a silo until processing.

The Renescience technology applied in this example comprised three steps.

The first step was a mild heating (pre-treatment) of the MSW by hot water to temperatures in the range of 40-75° C. for a period of 20-60 minutes. This heating and mixing period opened plastic bags and provided adequate pulping of degradable components preparing a more homogenous organic phase before addition of enzymes. Temperature was adjusted in the heating period to the optimum of isolated enzyme preparations which was used for enzymatic hydrolysis. Hot water was added as clean tap water or as washing water first used in the washing drums and then recirculated to the mild heating step.

The second step was enzymatic hydrolysis and fermentation (liquefaction). The enzymatic liquefaction and fermentation was performed continuously at a residence time of app. 12-18 hours, at the optimal temperature and pH for enzyme performance. By this hydrolysis and fermentation the biogenic part of the MSW was liquefied into a bioliquid.

The third step of Renescience technology as practiced in this example was a separation step where the bioliquid was separated from the non-degradable fractions. The separation was performed in a ballistic separator, washing drums and hydraulic presses. The ballistic separator separated the enzymatic treated MSW into the bio-liquid, a fraction of 2D non-degradable materials and a fraction of 3D non-degradable materials. The 3D fraction (physical 3 dimensional objects as cans and plastic bottles) did not bind large amounts of bioliquid, so a single washing step was sufficient to clean the 3D fraction. The 2D fraction (textiles and foils as examples) bound a significant amount of bioliquid. Therefore, the 2D fraction was pressed using a screw press, washed and pressed again to optimize the recovery of bio-liquid and to obtain a "clean" and dry 2D fraction. Inert material which was sand and glass was sieved from the bioliquid by subjecting it to further "fine" separation using two vibrating sieves, the first having 8 mm sieves, which separated out primarily non-degradable contaminants. The second vibrating sieve, having 3 mm sieves, separated out larger fibers, which comprised a considerable amount of bio-degradable material.

The waste, with added enzymes, was incubated in a reactor termed a "bioreactor" similar to that described in WO2011/032557, featuring a chamber that rotated on a substantially horizontal axis, equipped with attachments on its inner surface that formed a spiral array, which moved MSW continuously from the input to the output end. Depending on the degree to which the reactor was filled, and depending on the size of the reactor, the average "residence time" of MSW within the reactor was controlled. The reactor was equipped with heating elements such that an appropriate temperature could be maintained. While continuously introducing MSW into the reactor and continuously removing partially degraded MSW from the reactor, a certain average residence time was obtained.

Unsorted MSW was loaded continuously in to the Renescience demo plant. The isolated enzyme preparation used was a commercially available cellulase preparation optimized for conversion of lignocellulosic biomass and provided by NOVOZYMES™ under the trade name CELLIC CTEC 3™. For periods in which isolated cellulase preparation was used, an amount corresponding to 9 g of enzyme preparation was added for each kg of incoming MSW (0.9% by weight). It is believed that similar results would be obtained using other commercially available enzyme preparations, such as Cellic CTec2™ (Novozymes A/S) and ACCELLERASE 1500™ (Genencor). Simpler isolated cellulase preparations may also be effectively used to practice methods of the invention.

The settings for the operation were as follows:
- Introduced an incoming MSW stream into the enzyme reactor at the rate 280 kg MSW/h.
- Adjusted the non-water content of the incoming MSW stream by adding a solution of recirculated wash water, which had been stored in the buffer tank at ambient temperature, then heated to approximately 75 degrees C. in the water heater at the rate of 560 L water/h.
- Introduced CTEC 3™ to the incoming MSW stream at 0.9% by weight corresponding to cellulase activity of approximately 670 FPU per L water content of the wetted MSW.
- Run the enzyme reactor so as to achieve an average retention time of approximately 12-18 hours at approximately 50 degrees C.

The produced bioliquid was used for biomethane production in a pilot scale anaerobic digester Shear Enhanced Anaerobic Digestion (SEAD) at the Technical University of Denmark. The pilot-scale CSTR (Continued Stirred Tank Reactor) was a mobile SEAD anaerobic digester provided by VEOLIA/Biothane™. The SEAD anaerobic digester was a 500 Liter tank (Ø0.6×2.1 m) where the biological conversion took place. The main tank was mixed due to the reinjection of the biogas at the bottom of the reactor (230 L/h) and a recirculation pump (2-6 m3/h). The recirculated liquid was reinjected through a nozzle, which applied shear forces and facilitated the disintegration of particulate matter. The effluent was discharged by overflow to a settling tank (Ø0.25×0.8 m) where sludge and water were passively separated. The feedstock was stored in a 100 Liter tank, which was constantly agitated. A 5 mm mesh prevented the introduction of too large particles into the feed tank.

The Raw Digestate (RD) from anaerobic digestion periods with stable biogas production was collected in 100 L drums and stored in a freezer at −18 degrees Celcius until needed for further testing.

The frozen Raw Digestate drums from the anaerobic digestion were defrosted by leaving at room temperature for 2 days and subsequently mixed thoroughly.

The Raw Digestate was centrifuged in a laboratory scale centrifuge Thermo Scientific SL40R centrifuge in 750 mL containers at 4700 rpm for 15 minutes for phase separation into a water phase centrate with an approximate dry matter content of 0.5-1.5% w/w and a solid digestate phase with an approximate dry matter content of 25-30% w/w (termed Solid Digestate and abbreviated SD).

The solid digestate was dried at 105 degrees C. until constant mass (termed Dried Digestate and abbreviated DD) resulting in hard, unworkable lumps. It was, therefore, necessary to mill the dried digestate. This was done on a fritisch pulverisette 9 at 1100 rpm in 30 seconds for production of brick discs (to match the particle size distribution of brickwork clay) as described in Example 3 (abbreviated DD milled for 30 seconds) and for production of Lightweight Aggregates (to obtain a particle size<0.5 mm) as described in Example 5 (abbreviated DD 0.5 mm).

Dewatered Digestate was burned to Digestate Ash (DA) in an oven, increasing the temperature from room temperature to 950 degrees C., holding at 950 degrees C. for 2 hours and cooling to room temperature. Burning of digestate at 950 degrees C. resulted in fragile, porous lumps of redish color. After mixing the ashes, the ash was milled in order to be utilized as a partial cement replacement. Milling was done on a fritisch pulverisette 9 at 1100 rpm in 15 seconds.

Example 2. Characterization of Digestate, Sewage Sludge and Coal Fly Ash

Loss on ignition (550 degrees C. and 950 degrees C.): Loss on ignition as measured in accordance with (DS/EN 196-2 2005) at both 550 degrees C. and 950 degrees C. Loss on ignition at 550 degrees C. describes the content of organic matter, and loss on ignition at 950 degrees C. further describes the ignition of barium sulphate and other insoluble residues (DS/EN 196-2 2005).

Conductivity and pH: The conductivity was measured in a 1:2.5 solid to liquid ratio suspension in distilled water with an electrical conductivity meter. pH was measured in the suspension with a pH electrode.

Water Content: Measured as weight loss at 105 degrees C.

Content of chloride and sulphate: Dried sample (10.0 g) was suspended in 25.0 mL distilled and agitated for 1 hour. The concentration of chloride and sulphate were measured in the filtrate by Ion Chromatography.

Particle size distribution: The particle size distribution was measured on the solid digestate, dry dried digestate, and digestate ash by laser diffraction by the use of Mastersizer 2000.

Morphology: The morphology is evaluated by Scanning Electron Microscope (SEM). The SEM analysis is performed directly at a small ash sample on a tape.

Mineralogy: The content of minerals was analysed by X-ray diffractions (XRD) (PanAlytical X-ray diffractometer).

TGA. (Thermogravimetric analysis, instrument: NETZSCH STA 449F3). RANGE: 29 degrees C./10.0 (K/min)/1050 degrees C.

Carbonate content: Determined by the volumetric calcimeter method.

Water solubility: The solubility was determined: 50.0 g ash was suspended in 500 mL distilled water. The suspension was shaken for 1 min. and the water decanted. New 500 mL of distilled water was added. This was repeated three times. Finally, the suspension was filtered and the ash dried and weighed.

Physical and Chemical Characteristics of Digestate

The mean values and standard deviations for the chemical and physical characteristics of digestate (on SD and DD basis) measured at DTU (Technical University of Denmark) are listed in Table 1.

TABLE 1

Chemical and physical characteristics of digestate. ± defines the standard deviation (DD = Dried Digestate and SD = Solid Digestate). 1 and 2 refers to the batch of digestate.

| Parameter | | Test performed on |
|---|---|---|
| $Cl^-$ (%w/w) | 0.3 ± 0.0 | $DD_1$ |
| $SO4^{-2}$ (%w/w) | 0.2 ± 0.0 | $DD_1$ |
| LoI, 550 degrees C. (%w/w) | 59.7 ± 0.2 | $DD_1$ |
| LoI, 950 degrees C. (%w/w) | 64.1 ± 0.2 | $DD_1$ |
| Conductivity (mS $cm^{-1}$) | 5.6 ± 0.1 | $SD_1$ |
| Water content (% w/w) | 74.1 ± 0.02 | $SD_1$ |
| Carbonate content (% w/w) | 9.2 ± 0.6 | $DD_2$ |

The content of anions in the digestate was less than 1% per weight (for chloride and sulphate), and this concentration was not considered an obstacle for utilization of digestate. A high salt content would result in efflorescence at both bricks and LWA.

Morphology

The morphology of both SD and DD (milled for 30 seconds) was investigated by SEM-analysis, see FIG. 1, where a) SD magnified 200 times, b) SD magnified 1500 times, c) DD magnified 200 times and d) DD magnified 1500 times. In a) and b) in FIG. 1, the solid digestate is more clustered, compared to the dewatered digestate shown in c) and d) in FIG. 1, which is more divided into separate particles.

Mineralogy

Figure 2:
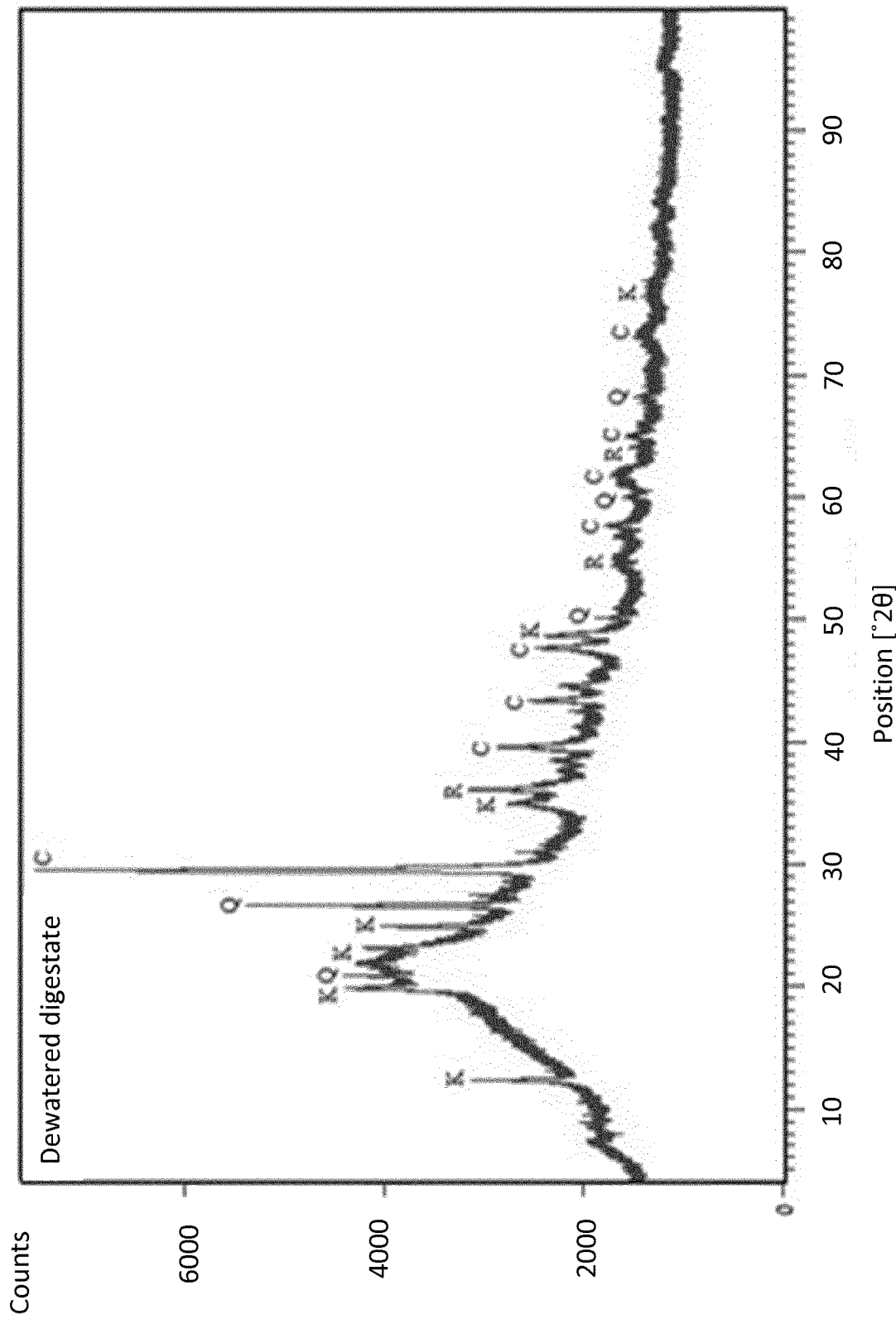
FIG. 2. X-ray diffraction (XRD) diffractograms for Dried Digestate (DD). K-Kaolinite ($Al_2Si_2O_5(OH)_4$), Q-Quartz ($SiO_2$), C-Calcite ($CaCO_3$) and R-Rutile ($TiO_2$).

The mineralogy of the digestate was measured by XRD-diffraction for DD, see diffractogram in FIG. 2. The program X'Pert HighScore Plus was used for data treatment. The minerals kaolinite (K), quartz (Q), calcite (C) and rutile (R) were identified in DD. A semi-quantitative analysis resulted in the relative abundance: C>Q>K>>R for DD.

Kaolinite is a clay mineral contributing to sintering of the material, thus the content of kaolinite in DD could have a positive impact on the utilization of digestate in bricks and LWA by contributing to the sintering. Note that sintering is a process below the melting point of the material facilitating cohesion. Rutile is commonly used as a glaze for pottery, which could lead to a slight blue contribution to the colour of the fired bricks. It should be noted, that rutile represents a very small part of the minerals detected in the digestate, thus a discolouring of the bricks is not expected.

Based on the mineralogy, bricks and LWAs produced with digestate are not expected to be contaminated with unwanted minerals, but instead the digestate contains minerals, which could have a positive effect on the durability of the fired bricks.

Characterization of Sewage Sludge Digestate

A sewage sludge digestate was used in building material experiments as a reference material since sewage sludge additions in building materials previously have been reported in literature and in the industry. The sewage sludge is from an urban waste water treatment facility where the treated sewage sludge is partly converted to biomethane in an anaerobic digester. The sewage sludge raw digestate from the biogas plant was dewatered at the waste water facility to a dry matter content of about 20-25% w/w. A sample of dewatered sewage sludge digestate was obtained and stored in freezer at minus 18 degrees C. until needed for the building material experiments.

Some characteristics of the sewage sludge is listed in Table 2. It was seen that the Loss on Ignition (LoI) at both 550 degrees C. and 950 degrees C. and water content are similar to the measures for digestate. The carbonate content of the sewage sludge (2.2% w/w) was less than the for the digestate (9.2% w/w) (cf. Table 1 and 2).

TABLE 2

Chemical and physical characteristics of sewage sludge

| Parameter | | Test performed on |
|---|---|---|
| LoI, 550 degrees C. (% w/w) | 63.4 ± 0.1 | Dried sample |
| LoI, 950 degrees C. (% w/w) | 65.5 ± 0.03 | Dried sample |
| Conductivity (mS cm$^{-1}$) | 3.1 | As received sample |
| Water content (% w/w) | 77.7 ± 0.09 | As received sample |
| Carbonate content (% w/w) | 2.2 ± 0.2 | Dried sample |

Thermal Analysis of Digestate and Sewage Sludge

Figure 3:
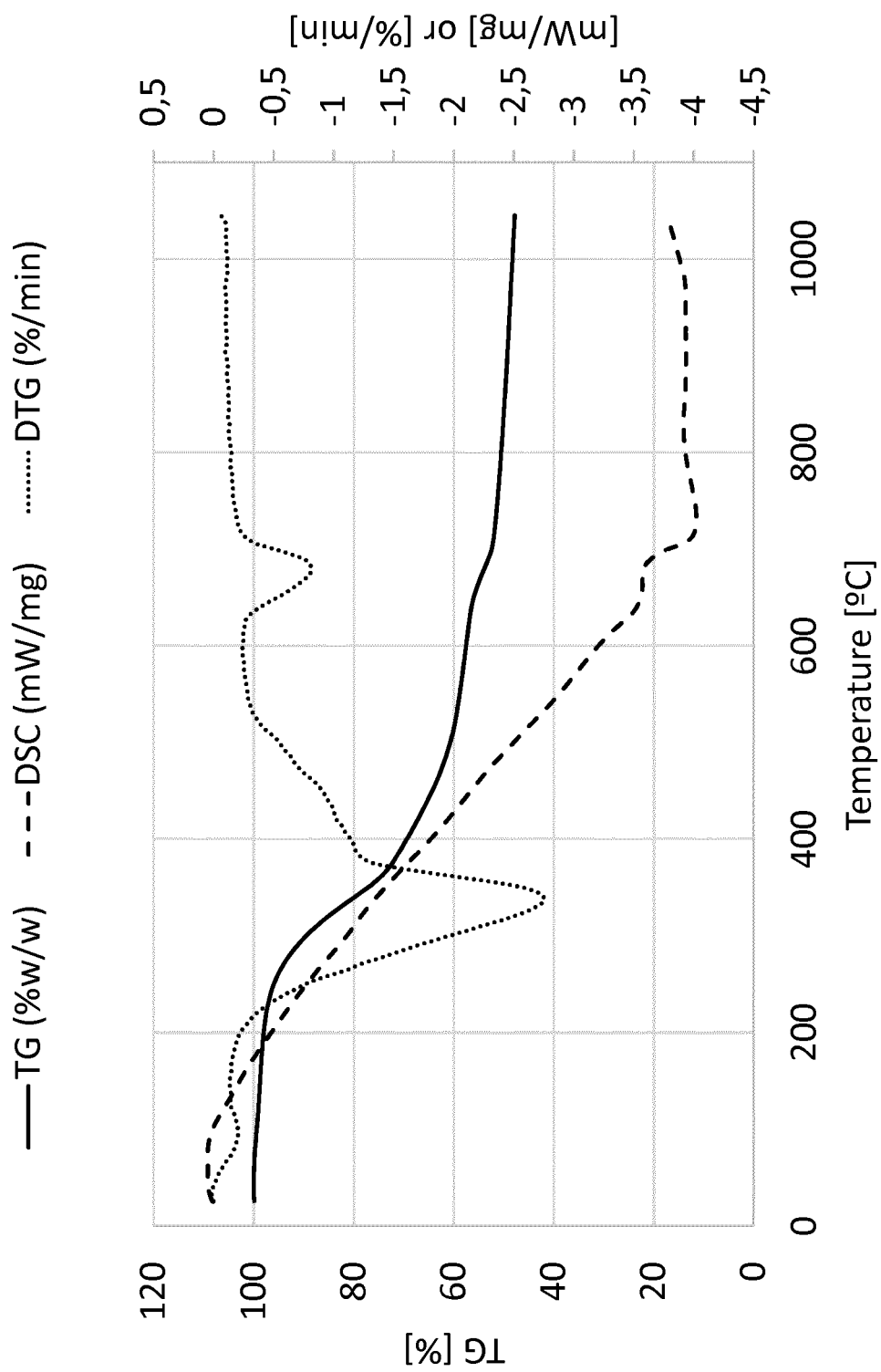
FIG. 3 TGA result for DD (DSC=differential scanning calorimetry, TGA=thermogravimetric analysis, DTG=derivative thermogravimetry).
Figure 4:
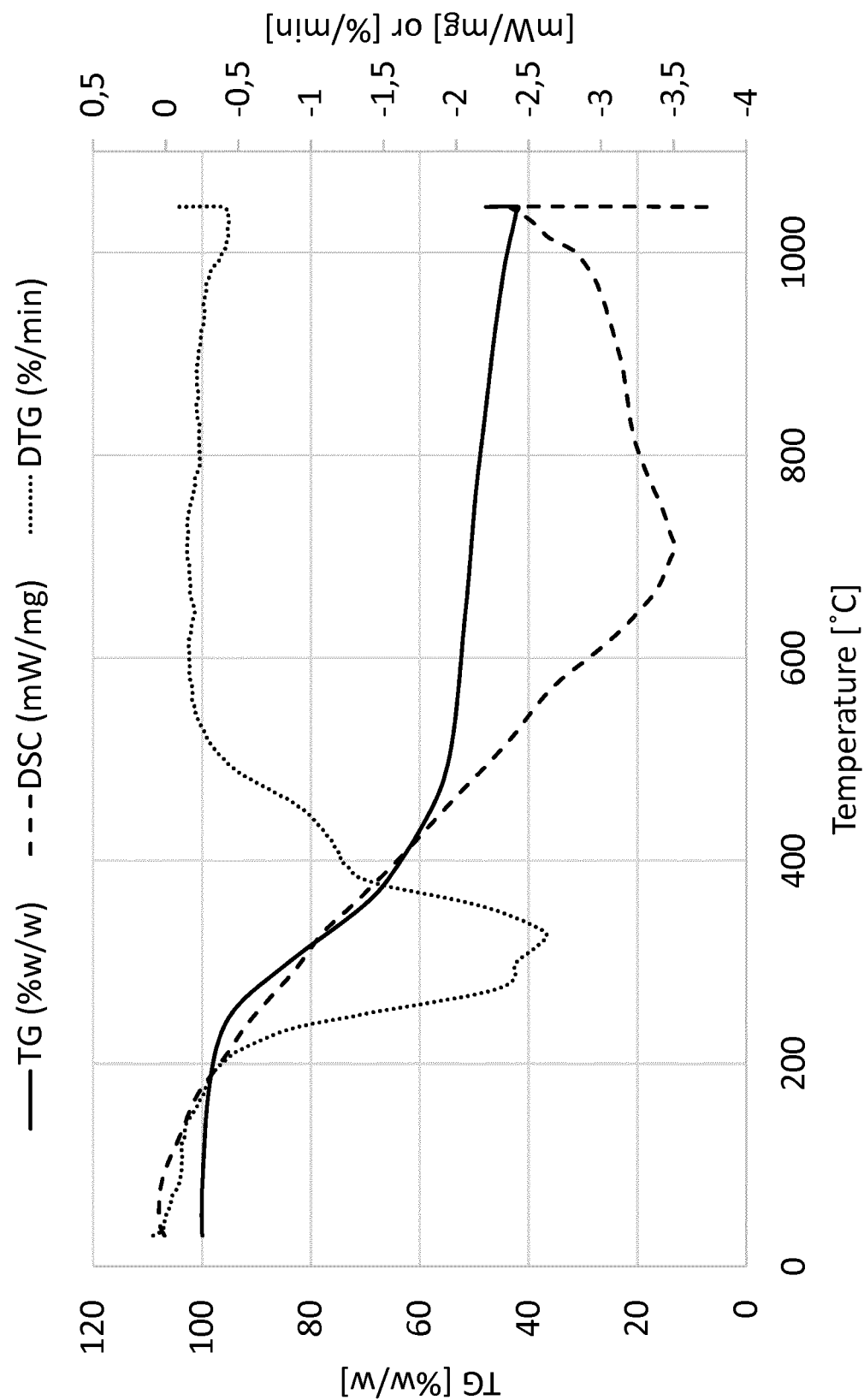
FIG. 4 TGA result for Sewage Sludge digestate (SS) (DSC=differential scanning calorimetry, TGA=thermogravimetric analysis, DTG=derivative thermogravimetry).

The results from the Thermogravimetric analysis (TGA) of the Dried Digestate (DD) and dried Sewage Sludge (SS) are shown in FIG. 3 and FIG. 4, respectively. The combined thermogravimetric (TG) and derivative thermogravimetric (DTG) curves with SS of the present investigation shows different zones:
- 20-200 degrees C.: Slow decrease in TG weight loss (about 3%)
- 220-550 degrees C.: Peak in DTG (maximum at 326 degrees C.) The peak seems as a double peak. Steep decrease in TG. At around 400 degrees C., the slope of the curves changes to less steep. A change towards steeper is seen again around 450 degrees C.
- 550-1050 degrees C.: DTG almost constant and almost linear decrease in TG from 52 to 42% (the residual mass).

The combined TG and DTG with DD of the present investigation shows different zones:
- 20-200 degrees C.: Slow decrease in weight loss (about 2%)
- 220-550 degrees C.: Peak in DTG (maximum at 337 degrees C.) and steep decrease in TG. At around 400 degrees C., the slope of the curves changes. A change is seen again around 450 degrees C.
- 550-620 degrees C. Slight decrease in TG and constant DTG
- 620-700 degrees C. Steeper slope at TG and peak at DTG (681 degrees C.)
- 1050 degrees C.: DTG almost constant and an almost linear decrease in TG from 53 to 48% (the residual mass).

Hernandez et al. (Thermal decomposition of sewage sludge under N2, CO2 and air: Gas characterization and kinetic analysis, *Journal of Environmental Management*, 2017) reports three zones when performing thermogravimetric analysis with sewage sludge: 50-200 degrees C.: Moisture loss during drying. 200-400 degrees C.: Decomposition of biodegradable organics>400 degree C.: Degradation of non-biodegradable organics.

In comparison to this, the first phase of the present two TGA analyses is expected to be caused by moisture loss and drying. The major peaks at 337 degrees C. and 326 degrees C. for the DD and SS, respectively, may relate to decomposition of biodegradable organics, while the change in slope of the DTG curve at around 400 degrees C. reflects a change towards degradation of non-biodegradable organics. The peak at around 681 degrees C. at the DTG graph for DD is expected to represent $CaCO_3$ as identified by XRD.

Particle Size Distribution

Figure 5:
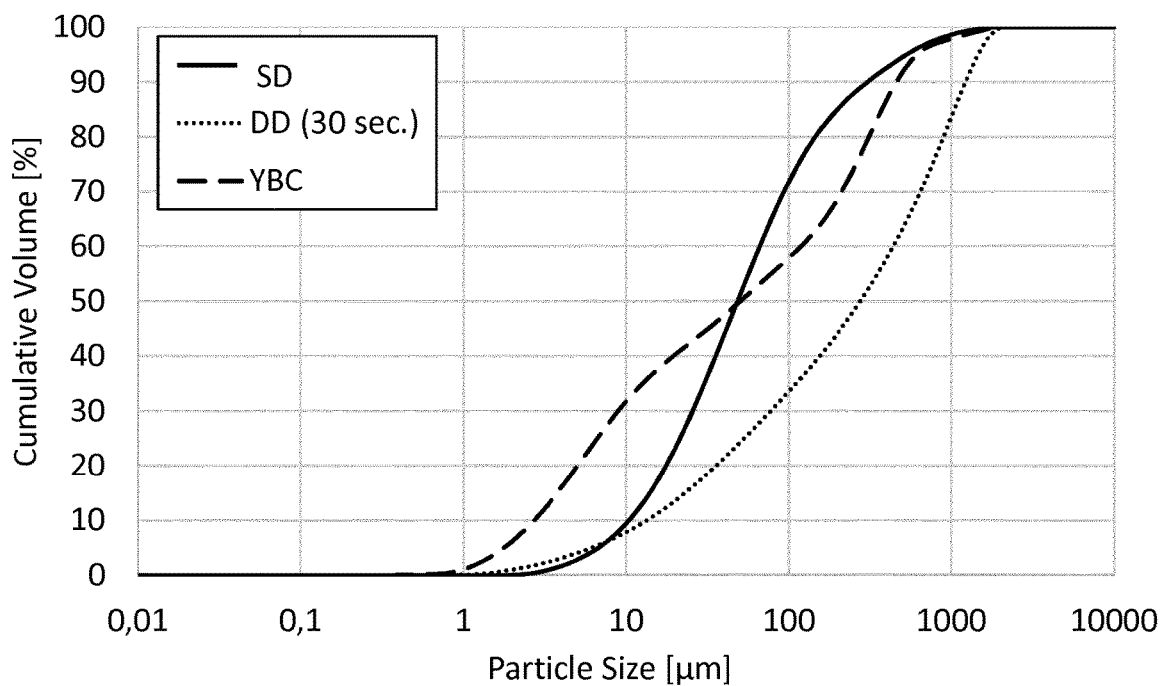
FIG. 5. Particle size distribution of Solid Digestate (SD) and Dried Digestate (DD) (milled for 30 seconds).

The particle size distribution was measured for SD, DD (milled for 30 seconds) and YBC for utilization in bricks, see FIG. 5.

SD had a more even particle size distribution than DD (milled for 30 seconds), see FIG. 5, which could lead to a better packing arrangement of the particles, thus a better sintering of the raw material, when utilized for brick production. The $d_{50}$ of SD further corresponded better to $d_{50}$ of YBC compared to DD (milled for 30 seconds), see Table 3. The high value of $d_{50}$ obtained for DD (milled for 30 seconds) is due to a larger particle size average, which is a result of drying the digestate at 105 degrees C., causing the digestate to lump together and thus subsequently milling is needed.

TABLE 3

Mean particle size, clay, silt and sand fraction for SD, DD (milled for 30 seconds) and YBC.

| | SD | DD (milled for 30 seconds) | YBC |
|---|---|---|---|
| Mean particle size, $d_{50}$ (μm) | 48.5 | 276.1 | 50.5 |
| Clay fraction (%) | 0.0 | 1.0 | 6.2 |
| Silt fraction (%) | 58.3 | 26.2 | 46.3 |
| Sand fraction (%) | 41.6 | 72.8 | 47.4 |

SD, DD (milled for 30 seconds) and YBC were divided into the clay (<2 μm), silt (2-63 μm) and sand fractions (63-2000 μm) based on the particle size distribution, see Table 3. The fractions obtained for SD were more in conjunction with the fractions of YBC, compared to the fractions of DD (milled for 30 seconds). The sand fractions for DD (milled for 30 seconds) were significantly higher, compared to the sand fraction for SD and YBC, substantiating the observation from $d_{50}$ of DD (milled for 30 seconds) obtaining a larger average particle size as a result of drying the digestate at 105 degrees C. and subsequently milling. Additional milling to smaller particle sizes is therefore expected to further improve brick quality through improved sintering.

By utilizing the initial water content of the digestate (SD) directly, a more even particle size distribution and the $d_{50}$ and division into fractions alike YBC is expected. This could lead to a better sintering when utilized as a partial replacement of clay for brick production, thus improving the durability of the fired bricks.

Atterberg Limits

The plastic limit, liquid limit and plasticity index from Atterberg's tests are shown in Table 4.

TABLE 4

Atterberg limits for YBC and KA

| | Plastic limit [%] | Liquid limit [%] | Plasticity Index [%] |
|---|---|---|---|
| YBC 0% DD | 13.5 | 22.4 | 8.9 |
| YBC 10% DD | 17.6 | 26.3 | 8.6 |
| YBC 20% DD | 21.9 | 29.8 | 7.9 |
| YBC 30% DD | 25.9 | 33.2 | 7.3 |
| KA 0% DD | 24.7 | 39.1 | 14.4 |
| KA 10% DD | 26.4 | 37.6 | 11.2 |
| KA 20% DD | 27.5 | 37.9 | 10.4 |
| KA 30% DD | 30.1 | 39.9 | 9.9 |

The results from the Atterberg limits were used for determination of the mix designs of the LWA and the brick discs.

Characterization of Digestate Ash

Table 5 summarizes the result from the characterization of DA compared to Coal Fly Ash (CFA). CFA is a by-product from combustion of powdered coal at thermal power plants. Today, CFA is utilized as a mineral admixture facilitating the strength development through pozzolanic reactions (Mehta, P. K., 2006. Concrete: structure, properties, and materials, McGraw-Hill). The standard for evaluating fly ash as a mineral admixture is (DS/EN 450-1 2012).

TABLE 5

Chemical and physical characteristics of the digestate-ash and limits according to (DS/EN 450-1 2012), values for CFA according to the literary review. ± defines the standard deviation.

|  | DA | (DS/EN 450-1 2012) | CFA - literary review* |
|---|---|---|---|
| Chemical composition | | | |
| $SiO_2$ (%) | 33.4 | >25.0 | 26.0-60.3 |
| $Al_2O_3$ (%) | 11.9 | | 10.6-28.1 |
| $Fe_2O_3$ (%) | 7.6 | | 4.0-15.71 |
| Σ (primary oxides) | 52.9 | >70.0 | 40.6-100 |
| CaO (%) | 23.1 | <10.0 | 2.0-16.6 |
| MgO (%) | 3.5 | <4.0 | 0.89-2.8 |
| $K_2O$ (%) | 2.5 | | 0.2-4.43 |
| $Na_2O$ (%) | <0.5 | | 0.2-4.3 |
| $TiO_2$ (%) | 0.6 | | 0.5-1.2 |
| $SO_3$ (%) | 1.7 | <3.0 | 0.3-6.2 |
| $Cl^-$ (%) | 0.0 ± 0.0 | <0.1 | |
| $SO_4^{-2}$ (mg/kg) | 5,930 ± 433 | | |
| LoI, 550 degrees C. (%) | 0.11 ± 0.03 | | |
| LoI, 950 degrees C. (%) | 0.67 ± 0.12 | <9.0 | 0.4-10.4 |
| Physical properties | | | |
| Mean particle size, $d_{50}$ (μm) | 19.6 | | 3.74-31.3 |
| Specific Surface Area ($m^2$/kg) | 0.862 | | 0.2-0.7 |
| pH | 11.7 ± 0.05 | | 10.4-13.5 |
| Conductivity (mS $cm^{-1}$) | 4.4 ± 0.2 | | |
| Solubility (%) | 2.9 ± 0.3 | | 3.5-79 |

*Mehta, P. K., 2006. Concrete: structure, properties, and materials., McGraw-Hill. Chindaprasirt, P. et al., 2009. Comparative study on the characteristics of fly ash and bottom ash geopolymers, Waste Management, 29(2), pp. 539-543. Donatello, S., Tyrer, M. & Cheeseman, C. R., 2010. Comparison of test methods to assess pozzolanic activity. Cement and Concrete Composites, 32(2), pp. 121-127. Goodarzi, F., 2006. Characteristics and composition of fly ash from Canadian coal-fired power plants. Fuel, 85(17-18), pp. 2683-2684. Oner, A., Akyuz, S. & Yildiz, R., 2005. An experimental study on strength development of concrete containing fly ash and optimum usage of fly ash in concrete. Cement and Concrete Research, 35(6), pp. 1165-1171. Wong, J. W. C. & Wong, M. H., 1990. Effects of fly ash on yields and elemental composition of two vegetables, Brassica parachinensis and B. chinensis. Agriculture, Ecosystems & Environment, 30(3-4), pp. 251-264. Ghosal, S. & Self, S. A., 1995. Particle size-density relation and cenosphere content of coal fly ash. Fuel, 74(4), pp. 522-529. Lee, S. H. et al., 2003. Effect of particle size distribution of fly ash-cement system on the fluidity of cement pastes. Cement and Concrete Research, 33(5), pp. 763-768. Kosmatka, S. H., Kerkhoff, B. & Panarese, W. C., 2002. Design and Control of Concrete Mixtures, Portland Cement Association. Sear, L. K., 2001. Properties and use of coal fly ash: a valuable industrial by-product, Gray Publishing. Henry, W. M. & Knapp, K. T., 1980. Compound Forms of Fossil Fuel Fly Ash Emissions. Environmental Science and Technology, 14(4), pp. 450-456.

A content of primary oxides>70% is necessary in order for an admixture to be categorized as a pozzolan according to (ASTM International C618-15 2010). DA had a total content of primary oxides of 52.9%. Thus, DA did not contain enough primary oxides, in order to enter the necessary amount of pozzolanic reactions to contribute to a sufficient increase in the compressive strength when DA was used as a partial cement replacement. However, it should be noted that several other factors influence the contribution to the development of compressive strength from DA, e.g. the filler effect, thus a partial cement replacement with DA could still be beneficial.

A high pH-value is important for a cementitious mixture since hydrated cement exists in a state of equilibrium between the solid phase, consisting of relatively insoluble hydrates and a high-pH pore fluid. If the pH-value decreases to less than 11.5 it would destroy the passivity of the environment and e.g. start the corrosion process of any reinforcement (Mehta, P. K., 2006. Concrete: structure, properties, and materials, McGraw-Hill). Furthermore, a high pH-value promotes the dissolution of the glass particles in the ash, which alters into clay-like minerals, with same advantageous properties as clay, beneficial for e.g. the stability of a concrete structure (Zevenbergen, C. et al., 1999. Clay Formation and Metal Fixation during Weathering of Coal Fly Ash. Environmental Science & Technology, 33(19), pp. 3405-3409). A high pH-value of any admixture is therefore desirable, as it will contribute to the passivity of a cementitious mixture. The pH of DA was 11.7, which is within the limits for CFA, and thus this parameter is acceptable.

The conductivity of an admixture gives an indication of the amount of soluble ions in the admixture. A lower conductivity equals formation of more solid material when the ash is used in concrete, which is desirable as more solid material will be kept in a cementitious mixture when an admixture is added contributing to the compressive strength. However, the reactivity facilitates the pozzolanic reaction, which also contributes to the compressive strength. A conductivity of 4.4 is considered low, thus based on the conductivity DA are not considered particularly reactive. A low water solubility is preferable, as more solid material will be kept in the mixture and contribute to the compressive strength of the cured concrete. A water solubility of 2.89 is considered low, compared to the interval established for CFA.

Figure 6:
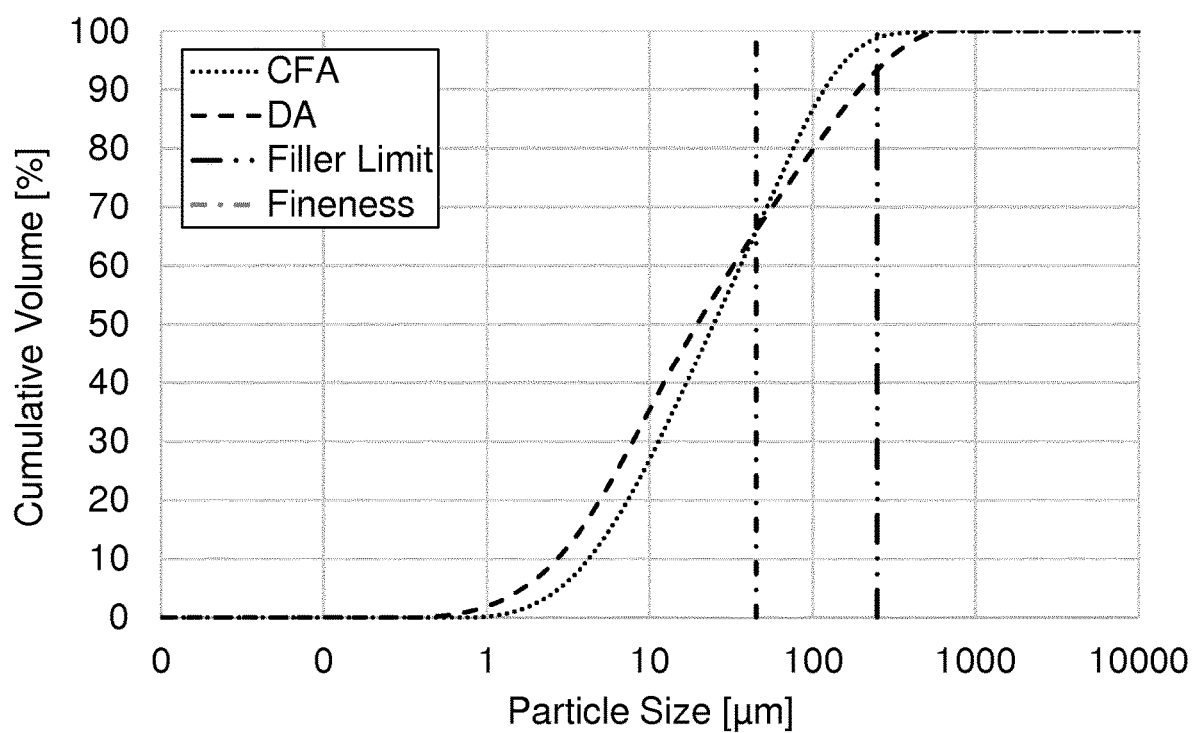
FIG. 6 Particle size distribution for Digestate Ash (DA) and Coal Fly Ash (CFA).

FIG. 6 shows the particle size distribution for DA. The particle size distribution for CFA was included for comparison, alongside the limit for Category N and the filler limit. Category N was a measure of the fineness of an ash. The fineness is defined in (DS/EN 450-1 2012) as the mass fraction in percent of an ash retained when sieved in a 45 μm mesh sieve. In order for the ash to comply with Category N, the fineness must be below 40%. The filler limit is defined as particles<250 μm (Herholdt, A. D. et al., 1985. Beton-Bogen (In Danish). Cementfabrikkernes tekniske oplysningskontor, Aalborg Portland, 2). The particle size distribution for DA was similar to the particle size distribution for CFA. The mean particle size, percentage complying with the filler limit and fineness for both DA and CFA are given in Table 6.

TABLE 6

Mean particle size, filler limit and category N for digestate ash and coal fly ash.

|  | DA | CFA |
|---|---|---|
| Mean particle size, $d_{50}$ (μm) | 19.6 | 24.7 |
| Fineness percentage complying with Category N limit (<45 μm), (%) | 34.0 | 34.1 |
| Percentage complying with the filler limit (<250 μm), (%) | 93.4 | 98.8 |

The fineness of DA complied with the fineness for CFA. DA further complied with Category N and no subsequently milling of the DA was therefore necessary, in order to utilize DA as a partial cement replacement.

About 93% of the DA complied with filler limit, thus is able to fill the intergranular voids between the cement grains, decreasing the porosity and increasing the compressive strength. Since only 6.6% of DA did not comply with the filler limit, no subsequently milling of the DA is necessary in order to utilize DA as a filler.

Figure 7:
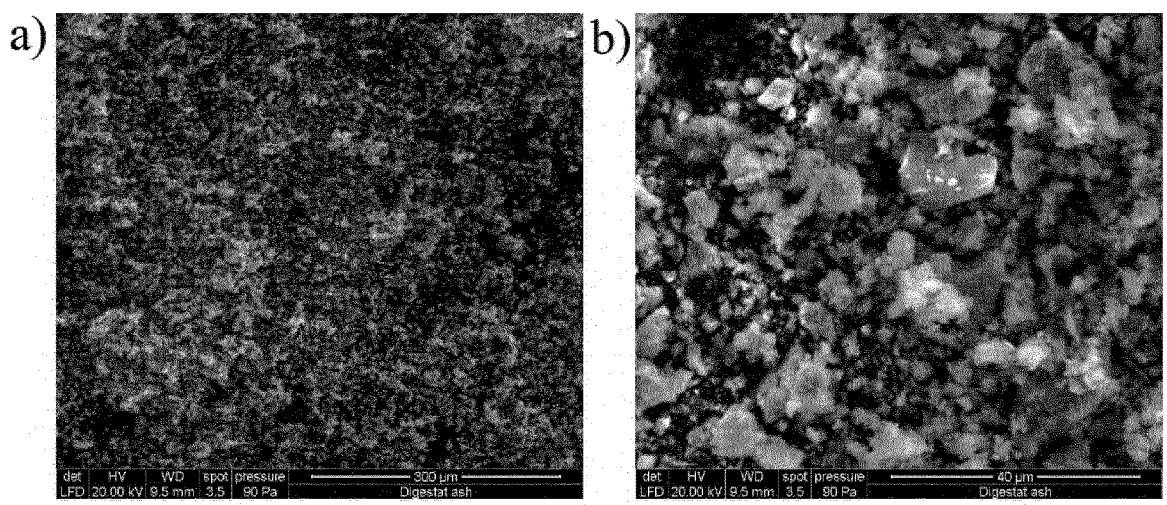
FIG. 7 SEM-analysis of DA; a) DA magnified 200 times and b) DA magnified 1500 times.

The morphology of DA was investigated by SEM-analysis, see FIG. 7, where a) DA magnified 200 times and b) DA magnified 1500 times. In a) and b) in FIG. 7, DA was seen to consist of angular particles and not rounded, as the particles of CFA. Coal fly ash in general mainly consisted of amorphous aluminosilicate spheres, and the chemical composition was different from that of DA.

Angular particles can facilitate various disadvantages compared to spherical particles. Angular particles require more water compared to round particles, thus it was necessary to add extra water to a cementitious mixture with angular particles in order to obtain the necessary workability. However, the addition of extra water has theoretically a decreasing effect on the compressive strength. In addition, angular particles do not fill the intergranular voids between the cement grains as well as rounded particles, and the ability to contribute to the filler effect and subsequently the compressive strength was decreased.

The Digestate Ash (DA) was prepared in a laboratory furnace at 950 degrees C. as described in Example 1 which was below the melting point of the ash. Industrial firing conditions at higher temperatures are expected to influence the particle size and shapes towards spherical particles.

Example 3. Preparation and Mineralogy of Bricks

Brick specimens with digestate substitution were made for 0%, 10%, 20% and 30% replacements of Yellow Brick Clay (YBC) with dried digestate (DD) as given in Table 7. Torres, P. et al., 2009 (Incorporation of wastes from granite rock cutting and polishing industries to produce roof tiles. *Journal of the European Ceramic Society*, 29(1), pp. 23-30) demonstrated that initial tests conducted on small-scale brick discs were a useful screening tool for selecting the best compositions of a mixture of clay and waste. For this investigation, a similar approach was adopted, using the same disc size (20 mm).

Determination of the mix designs for mixtures containing dewatered YBC and dry digestate is based on the results for the liquid and plastic limits determined by Atterberg as described in Example 2. Two different water contents, one just above $w_P$ (1W) and one just below $w_L$ (2W), were investigated. 1W and 2W are calculated from the following equations:

$$1W = w_P((w_L - w_P) \cdot 0.25)$$

$$2W = w_L - ((w_L - w_P) \cdot 0.25)$$

Where: $w_P$=plastic limit according to the Atterberg limit, $w_L$=liquid limit according to the Atterberg limit. Demineralized water was used for the disc mixtures.

TABLE 7

Mix design of one disc (2 g dry material) containing 0%, 10%, 20% and 30% dewatered digestate with 2 different water contents. Water content just above the plasticity limit are denoted 1W and 2W is the water content just below the liquid limit

| Abbreviation | YBC [g] | DD [g] | Water [g] | Water content [% wet weight] |
|---|---|---|---|---|
| YBC 0% DD 1W | 2.0 | 0 | 0.37 | 15.76 |
| YBC 0% DD 2W | 2.0 | 0 | 0.51 | 20.20 |
| YBC 10% DD 1W | 1.8 | 0.2 | 0.49 | 19.78 |
| YBC 10% DD 2W | 1.8 | 0.2 | 0.64 | 24.10 |
| YBC 20% DD 1W | 1.6 | 0.4 | 0.63 | 23.91 |

TABLE 7-continued

Mix design of one disc (2 g dry material) containing 0%, 10%, 20% and 30% dewatered digestate with 2 different water contents. Water content just above the plasticity limit are denoted 1W and 2W is the water content just below the liquid limit

| Abbreviation | YBC [g] | DD [g] | Water [g] | Water content [% wet weight] |
|---|---|---|---|---|
| YBC 20% D 2W | 1.6 | 0.4 | 0.77 | 27.84 |
| YBC 30% DD 1W | 1.4 | 0.6 | 0.77 | 27.74 |
| YBC 30% DD 2W | 1.4 | 0.6 | 0.91 | 31.38 |

Production of Discs

The method for the production of discs was in accordance with (Belmonte, L. J. et al., 2016. Screening of heavy metal containing waste types for use as raw material in Arctic clay-based bricks. *Environmental Science and Pollution Research*). The discs were produced by uniaxial compression in a purpose-built pellet presser, (developed at Technical University of Denmark), placed in a load-controlled press (Instron 6022) and a maximum load of 10.5±0.04 kN (33.42 MPa). A total of 15 discs were produced from each mixture.

The discs were dried at 105 degrees C. for 24 h, cooled to room temperature. The firing curve for the discs were adapted from (Chen, Y. et al., 2011. Preparation of eco-friendly construction bricks from hematite tailings. *Construction and Building Materials*, 25(4), pp. 2107-2111); the furnace temperature was gradually increased at a heating rate of 6 degrees C./min from room temperature to 1000 degrees C., holding at 1000 degrees C. for 2 hours, cooled (turning off the oven) until 200-150 degrees C., moved from the oven to a desiccator and cooled to room temperature. The weights, diameters and heights of the discs were measured before and after drying as well as after firing.

Results

Colour

No colour differences were seen in the brick discs from 0 to 30% w/w DD substitution (visual inspection).

Geometric Drying and Firing Shrinkage

In brick manufacturing, shrinkage is critical for the brick manufacturing process. The final brick size should be well-defined and complying with standardized dimensions, irrespectively of the raw material mix used in the given production.

Producers are currently only able to accommodate material within defined shrinkage values due to plant costs. Operating with different sizes of moulds or dies, depending on raw material mixture, is undesirable.

To assess if mixing dry digestate with clay during production of brick discs influenced the expected shrinkage obtained when having clay bricks with 0% of dry digestate, the following comparative assays were performed, where height and diameter were measured, and dimensional shrinkage, after drying and firing, was calculated.

Average results for the variation of shrinkage in samples from each composition, after drying and firing, are shown in Table 8 and Table 9.

TABLE 8

Drying shrinkage by dimensional change for discs with 0-30% replacements of YBC with DD (30 sec.) and two water contents in relation to raw/wet dimensions. ± defines the standard deviation.

| | Raw dimensions [mm] | | Dimensions after drying [mm] | | Drying shrinkage [%] | |
|---|---|---|---|---|---|---|
| | Diameter | Height | Diameter | Height | Diameter | Height |
| YBC 0% DD 1 W | 20.38 ± 0.34 | 3.04 ± 0.88 | 20.10 ± 0.21 | 3.04 ± 1.3 | 1.39 | 0.0 |
| YBC 0% DD 2 W | 20.05 ± 0.00 | 3.03 ± 0.13 | 20.00 ± 0.00 | 3.03 ± 1.3 | 0.25 | 0.0 |
| YBC 10% DD 1 W | 20.13 ± 0.23 | 3.22 ± 0.80 | 20.00 ± 0.00 | 3.25 ± 0.00 | 0.65 | −0.93 |
| YBC 10% DD 2 W | 20.13 ± 0.23 | 3.47 ± 0.13 | 20.00 ± 0.00 | 3.50 ± 0.00 | 0.65 | −0.86 |
| YBC 20% DD 1 W | 20.00 ± 0.00 | 3.82 ± 0.22 | 20.08 ± 0.08 | 3.80 ± 0.12 | 0.4 | 0.52 |
| YBC 20% DD 2 W | 20.30 ± 0.25 | 3.98 ± 0.07 | 19.6 ± 0.34 | 3.67 ± 0.24 | 3.4 | 7.8 |
| YBC 30% DD 1 W | 20.35 ± 0.16 | 4.02 ± 0.53 | 20.08 ± 0.08 | 4.12 ± 0.10 | 1.3 | 2.5 |
| YBC 30% DD 2 W | 20.29 ± 0.10 | 4.23 ± 0.09 | 20.01 ± 0.10 | 4.17 ± 0.12 | 1.4 | 1.4 |

TABLE 9

Firing shrinkage by dimensional change for discs with 0-30% replacements of YBC with DD (30 sec.) and two water contents in relation to dried dimensions. ± defines the standard deviation.

| | Dimensions after firing [mm] | | Firing shrinkage [%] | |
|---|---|---|---|---|
| | Diameter | Height | Diameter | Height |
| YBC 0% DD 1W | 20.19 ± 0.11 | 3.07 ± 0.11 | −0.45 | −0.99 |
| YBC 0% DD 2W | 20.06 ± 0.10 | 3.27 ± 0.13 | −0.30 | −7.9 |
| YBC 10% DD 1W | 20.11 ± 0.10 | 3.42 ± 0.12 | −0.55 | −5.2 |
| YBC 10% DD 2W | 20.10 ± 0.12 | 3.51 ± 0.13 | −0.50 | −0.29 |
| YBC 20% DD 1W | 20.05 ± 0.10 | 3.82 ± 0.16 | 0.15 | −0.53 |
| YBC 20% DD 2W | 19.87 ± 0.12 | 3.91 ± 0.07 | −1.3 | −6.5 |
| YBC 30% DD 1W | 19.98 ± 0.09 | 4.04 ± 0.08 | 0.50 | 1.9 |
| YBC 30% DD 2W | 19.95 ± 0.11 | 4.14 ± 0.09 | 0.30 | 0.72 |

Conclusion

Geometric shrinkages were calculated based on the dimensions of the disks. The collected data suggest a minimal shrinkage.

The dimensional drying shrinkage when adding up to 30% w/w dried digestate is within a few percentages and is observed not to be correlated with the amount of digestate mixed with clay.

The firing shrinkage when substituting up to 30% w/w dried digestate is seen to be within the variation of firing shrinkage observed for the clay sample without digestate. It can therefore be concluded that both drying and firing shrinkages are not significantly affected by clay substitution with dried digestate up to 30% w/w, after being compared to bricks where substitution of clay with dry digestate is 0%, not compromising the manufacturing standards in brick industry.

Mineralogy

Figure 8:
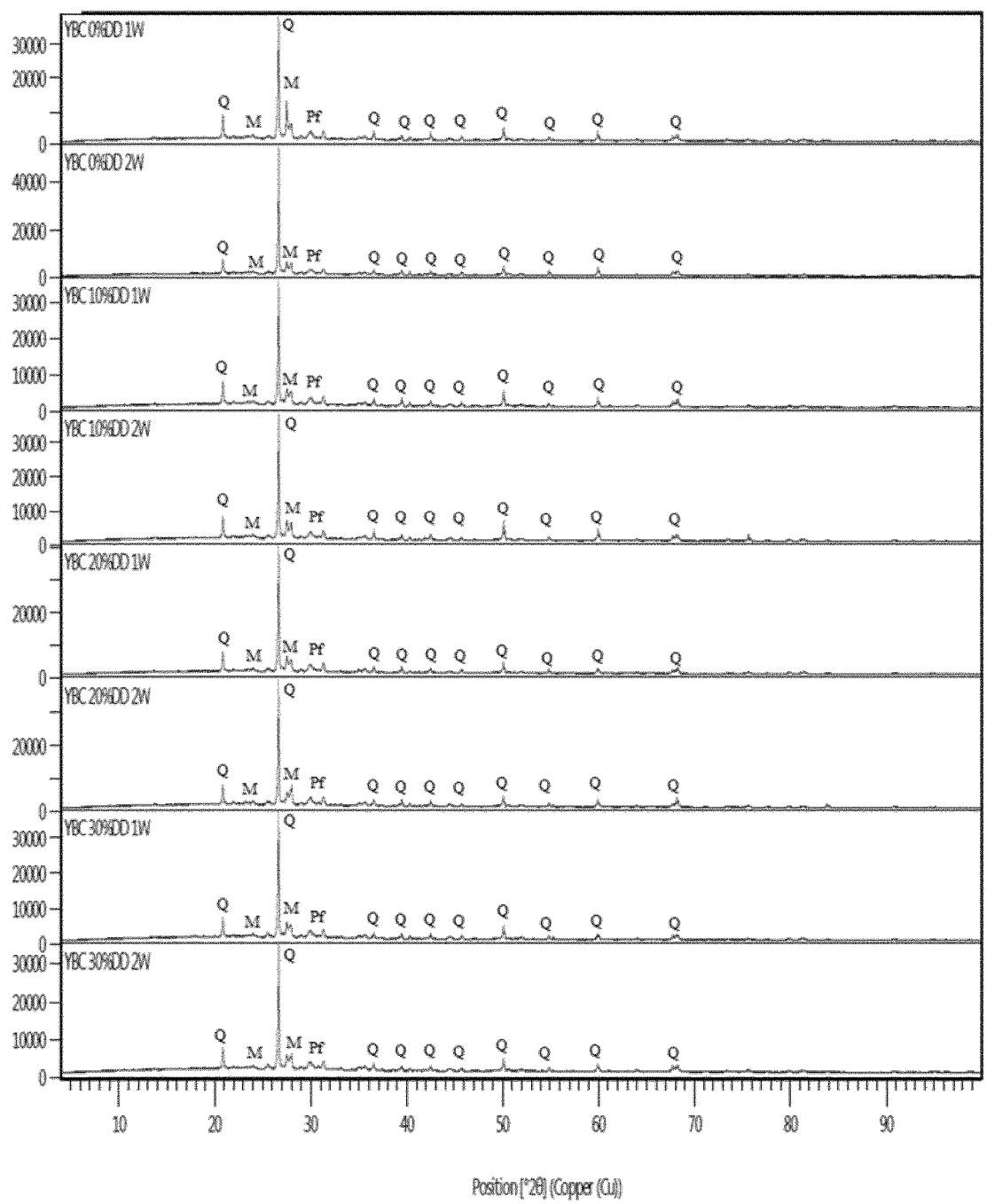
FIG. 8. X-ray diffraction (XRD) diffractograms for brick discs with 0-30% replacements of Yellow Brick Clay (YBC) with Dried Digestate (DD) (milled for 30 seconds). Q-Quartz ($SiO_2$), Pf-Plagioclase feldspar ($NaAlSi_3O_8$—$CaAl_2Si_2O_8$) and M-Microcline ($KAlSi_3O_8$).
Figure 9:
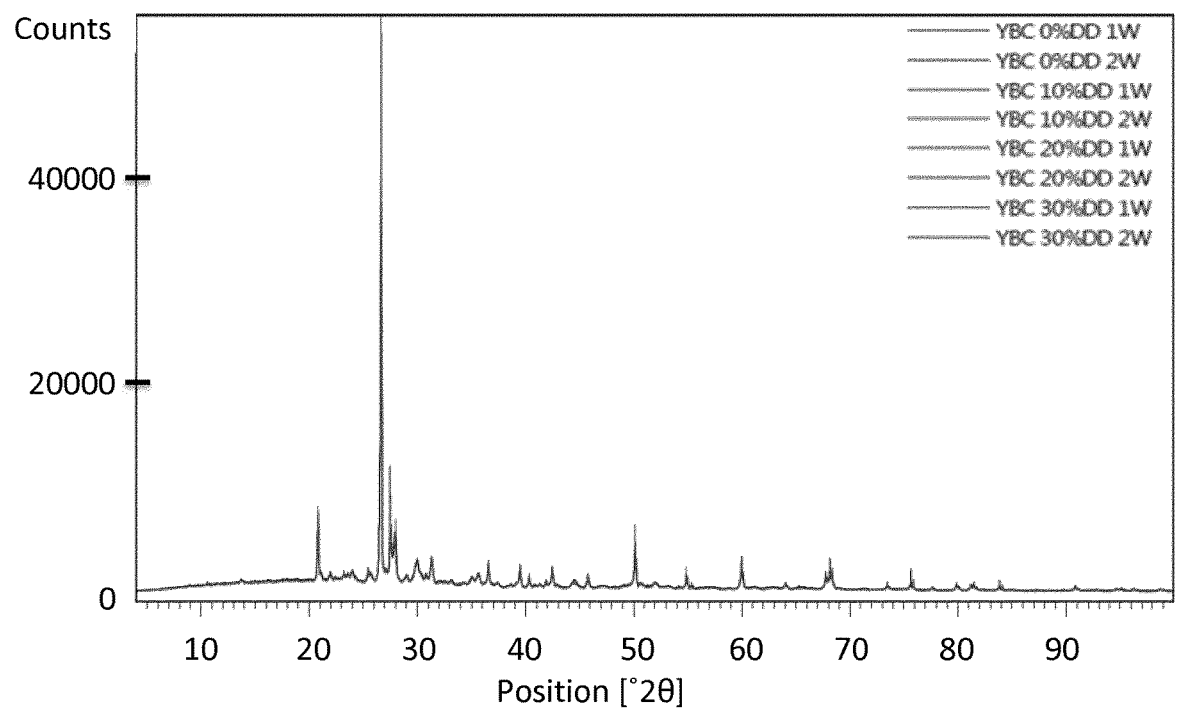
FIG. 9. X-ray diffraction (XRD) diffractograms for brick discs with 0-30% replacements of YBC with Dried Digestate (DD) displayed in one view.

The mineralogy was measured by XRD-diffraction for brick discs with 0-30% replacements of YBC with DD (milled for 30 seconds), see FIG. 8 and FIG. 9 and the program X'Pert HighScore Plus was used for data treatment.

The minerals quartz (Q), plagioclase feldspar (Pf) and microcline (M) were identified in all types of brick discs, both with and without DD (milled for 30 seconds), see FIG. 8. A semi-quantitative analysis was performed, arriving at Q>>Pf>M for all types of brick discs. Quartz, plagioclase feldspar and microcline are all minerals which are expected in red clay (Torres, P. et al., 2009. Incorporation of wastes from granite rock cutting and polishing industries to produce roof tiles. *Journal of the European Ceramic Society*, 29(1), pp. 23-30; Andersen, S. et al., 1989. Noget om ler, 5 artikler om sammenstning og brnding af ler til tegl. Miljøministeriet, Skov-og Naturstyrelsen, pp. 1-87).

The clay mineral kaolinite, quantified in the DD (milled for 30 seconds) above, was broken down during the firing and contributed to the sintering (Holmboe, T., 2001. Teglværksler i Danmark: sammensætningen af dansk teglværksler, hårdtbrændende ler, alternative lertyper og kortlægning med stang slingram. *Report (Geological Survey of Denmark and Greenland)*; Andersen, S. et al., 1989. Noget om ler, 5 artikler om sammenstning og brnding af ler til tegl. Miljøministeriet, Skov-og Naturstyrelsen, pp. 1-87) and calcite was considered to be subjected to high temperature decomposing, releasing $CO_2$, and contributing to the porosity (Cultrone, G. et al., 2004. Influence of mineralogy and firing temperature on the porosity of bricks. *Journal of the European Ceramic Society*, 24(3), pp. 547-564; Andersen, S. et al., 1989. Noget om ler, 5 artikler om sammenstning og brnding af ler til tegl. Miljøministeriet, Skov-og Naturstyrelsen, pp. 1-87). Thus, these are not quantifiable in the brick discs after firing at 1000 degrees C. Rutile is expected to constitute an unquantifiable part of the minerals in the brick discs, since the melting point of rutile is 1,843 degrees C., and thus would still be present.

XRD diffractograms for brick discs with 0-30% replacements of YBC with DD are displayed in one view, see FIG. 9. It is seen that all bricks discs arrive at the same XRD diffractogram, thus the digestate does not provide any problematic minerals, which could influence the mineral composition.

Example 4. Digestate Ash in Concrete

Digestate-Ash as a Partial Cement Replacement

Several studies have shown that use of different particulate materials can be used as partial cement replacement in mortar and concrete. For this investigation, the approach was to test digestate ash as partial cement replacement.

Previous studies have tested a variety of ash by-products, e.g. sewage sludge ash, wood ash and co-combustion ash and in general, no more than 5-10% replacements of cement with an alternative ash have shown feasible. Mortar samples had been produced with 5 and 10% cement replacements with digestate ash and mortar samples with 25% replacements were prepared for testing of the pozzolanicity. Furthermore, the properties of fresh mortar with both 5, 10 and 25% cement replacements were tested.

Determination of Mix Design

Determination of the mix designs for mortar with a partial cement replacement with DA was based on (DS/EN 196-1 2005). The mix design 0% cement replacement and a water to binder ratio w/b=0.5 (0% C 0.5) (Table 10) was in accordance with (DS/EN 196-1 2005). The subsequent mix designs where 0.5 was added to the abbreviation were calculated from this mix design corresponding to a water to binder-ratio (w/b-ratios, binder=content of cement and digestate-ash combined) of 0.5. Mix designs were made for 5%, 10% and 25% replacements of cement with DA.

After establishing the tendency for the flow values of mixtures with w/b=0.5, w/b-ratios for the second group of specimens was decided. The amount of DA replacing cement, varied according to the following equations:

$$\text{water content}_{5\% C} = 225 + \left(\frac{225}{100} \cdot 5\right) = 236.25 \text{g}$$

$$\text{water content}_{10\% C} = 225 + \left(\frac{225}{100} \cdot 10\right) = 247.5 \text{g}$$

$$\text{water content}_{25\% C} = 225 + \left(\frac{225}{100} \cdot 25\right) = 281.25 \text{g}$$

This second group of specimen was cast in order to test mortar with DA, which had a flow value as close to the reference as possible. The final mix designs are given in Table 10.

Materials used for the mixtures were:
CEM I: Rapid cement (CEM I 52.5 N (LA)) from Aalborg Portland. CEM I 52.5 N (LA) describes the cement as a Portland cement containing maximum 5% limestone. 52.5 N describes the minimum strength to be at least 20 MPa after 2 days of curing and 52.5 MPa after 28 days of curing. (LA) describes the alkali content to be approximate 0.6%.
DA: Milled for 15 sec.
Water: Demineralized water.
Sand: CEN Standard sand in accordance with (DS/EN 196-1 2005), consisting of rounded particles with a silica content of at least 98% and a particle size distribution ranging between 0-2 mm.

Production of Fresh Mortar and Mortar Specimens

The mixing and casting procedure of mortar samples were in accordance with (DS/EN 196-1 2005).

Mixing of Mortar

The mortar was mixed in a Hobart mixer, meeting the requirements of (DS/EN 196-1 2005). The mortar was mixed with the following procedure (DS/EN 196-1 2005):
Cement (and digestate-ash) were added to the bowl of the mixer.
Water was added at the time 0, and the mixer ran for 30 seconds at low speed.
Sand was added over 30 seconds.
The mixer was shortly stopped, switching from low to medium speed and turned on for 30 seconds.
The mixer was stopped for 90 seconds.
The mixer was turned on for 60 seconds.
After this procedure (4 min in total), the mortar was ready for testing or casting (as described below) and subsequently tested.

Casting Mortar Samples

The mortar samples were casted in moulds meeting the requirements of (DS/EN 196-1 2005), casting three specimens at a time pr. type of mixture.

When casting, the mixed mortar was poured into the mould until the mould was halfway full. The mould was

TABLE 10

Mix design of mortar samples containing 0%, 5%, 10% and 25% replacements of cement with digestate-ash with two different water contents to achieve water to binder w/b-ratios of 0.5 and a variation ratio (V) according to the flow values.

| Mix design | Abbrev. | CEM I [g] | DA [g] | Water [g] | Sand [g] | w/b-ratio |
|---|---|---|---|---|---|---|
| 0% cement replacement and water to binder ratio w/b = 0.5 | 0% C 0.5 | 450.0 ± 2 | 0 | 225.0 ± 1 | 1350 ± 5 | 0.5 |
| 5% cement replacement and w/b = 0.5 | 5% C 0.5 | 427.5 ± 2 | 22.5 | 225.0 ± 1 | 1350 ± 5 | 0.5 |
| 5% cement replacement and w/b variating (V) according to the workability. | 5% C V | 427.5 ± 2 | 22.5 | 236.25 ± 1 | 1350 ± 5 | 0.525 |
| 10% cement replacement and w/b = 0.5 | 10% C 0.5 | 405.0 ± 2 | 45 | 225.0 ± 1 | 1350 ± 5 | 0.5 |
| 10% cement replacement and w/b variating (V) according to the workability. | 10% C V | 405.0 ± 2 | 45 | 247.5 ± 1 | 1350 ± 5 | 0.55 |
| 25% cement replacement and w/b = 0.5 | 25% C 0.5 | 337.5 ± 2 | 112.5 | 225.0 ± 1 | 1350 ± 5 | 0.5 |
| 25% cement replacement and w/b variating (V) according to the workability. | 25% C V | 337.5 ± 2 | 112.5 | 281.25 ± 1 | 1350 ± 5 | 0.625 | vibrated on a vibrating table for 20 seconds. The mould was then filled to the top and vibrated again for 20 seconds.

The filled mould was covered with plastic and the specimens were left to set for 20-24 hours. After 20-24 hours, the specimens were demoulded and submerged in water for subsequently curing.

3×20 mortar samples were produced, as displayed in Table 11.

TABLE 11

Overview of mortar castings

| Specimen | Abbreviation | 7 days of curing | 28 days of curing | 90 days of curing |
|---|---|---|---|---|
| 0% cement replacement and water to binder ratio w/b = 0.5 | 0% C 0.5 | X | X | X |
| 5% cement replacement and w/b = 0.5 | 5% C 0.5 | X | X | |
| 5% cement replacement and w/b variating (V) according to the workability. | 5% C V | X | X | |
| 10% cement replacement and w/b = 0.5 | 10% C 0.5 | X | X | |
| 10% cement replacement and w/b variating (V) according to the workability. | 10% C V | X | X | |
| 25% cement replacement and w/b = 0.5 | 25% C 0.5 | X | X | X |
| 25% cement replacement and w/b variating (V) according to the workability. | 25% C V | X | X | X |

Properties of Fresh Mortar

The workability was tested according to (DS/EN 1015-3 1999) on a flow table and reported as the average flow value, a measurement of the fresh mortars ability to flow. The flow value was measured as the diameter of the mortar in two perpendicular directions. The average flow value was the average of four measurements, thus two samples must be performed for each mixture.

The setting process was measured by Vicatronic, according to (DS/EN 196-3 2009), where the initial setting time was defined as the time at which the distance between the needle and the baseplate of the specimen was 6±3 mm, and the final setting time was defined as the time where the needle only penetrated 0.5 mm into the specimen.

Properties of Mortar Specimens

Density of mortar specimens was measured before tensile and compression tests were conducted. The density was calculated according to the equation:

$$\text{Density} = \frac{W}{L \cdot b \cdot h}$$

Where:
W=weight [kg]
L=is the length of the mortar specimen [m]
b=is side of the square section of mortar specimen [m]
h=is the height of the mortar specimen [m]

The tensile strength of the mortar specimens was tested according to (DS/EN 196-1 2005) with an Instron 6022 three point bending machine. Tensile strength of each of the mix designs were calculated according to the equation:

$$B_f = \frac{1.5 \cdot F_f \cdot l}{b^2}$$

Where:
$R_c$=tensile strength [MPa]
l=distance between the supports [mm]
$F_f$=maximum load at fracture [N]
b=side of the square section of the mortar specimen [mm]

The compressive strength of the mortar specimen was tested according to (DS/EN 196-1 2005) on a Tony-300 testing machine. Statistical processing of the results was likewise done in accordance with (DS/EN 196-1 2005) and the compressive strength of each of the mix designs was calculated according to the equation:

$$R_c = \frac{F_c}{A_F}$$

Where:
$R_c$=compressive strength [MPa]
$F_c$=maximum load at fracture [N]
$A_F$=load area [mm]

The strength activity index is a measurement of the pozzolanic activity of an admixture, in this case, the digestate-ash. The index was calculated from the compressive strength at 28 and 90 days of mortar samples with a 25% replacement of cement with digestate-ash, according to the equation:

$$SAI = \left(\frac{A}{B}\right) \cdot 100$$

Where:
5AI=Strength Activity Index.
A=Compressive strength of mortar specimen with cement replacement at 28 or 90 days [MPa]
B=Compressive strength of mortar specimen without cement replacement at 28 or 90 days [MPa]

According to (DS/EN 450-1 2012) a mortar specimen with a 25% cement replacement must obtain 75% of the compressive strength of a mortar specimen without cement replacement at 28 days and 85% at 90 days if the admixtures possess pozzolanic activity. Converted into SAI, the SAI must exceed 0.75 at 28 days and 0.85 at 90 days (ASTM International C311-C311M 2005) if the admixtures possess pozzolanic activity.

Results

Workability

The average flow values for 0%, 5%, 10% and 25% cement replacements with two different water contents (w/b-ratio=0.5 and a variating w/b-ratio according to the content of digestate ash) are displayed in Table 12.

TABLE 12

Average flow values for 0%, 5%, 10% and 25% cement replacements with two different water contents (0.5 and variating according to the content of digestate ash).

| Mix design | Abbrev. | Average flow value [mm] | Deviation from reference [mm] | Deviation from reference [%] |
|---|---|---|---|---|
| 0% cement replacement and water to binder ratio w/b = 0.5 | 0% C 0.5 | 173.25 | — | — |
| 5% cement replacement and w/b = 0.5 | 5% C 0.5 | 163.25 | −10 | −5.8 |
| 5% cement replacement and w/b variating (V) according to the workability. | 5% C V | 175.75 | 2.5 | 1.4 |
| 10% cement replacement and w/b = 0.5 | 10% C 0.5 | 156.5 | −16.75 | −9.7 |
| 10% cement replacement and w/b variating (V) according to the workability. | 10% C V | 177.5 | 4.25 | 2.5 |
| 25% cement replacement and w/b = 0.5 | 25% C 0.5 | 130.75 | −42.5 | −24.5 |
| 25% cement replacement and w/b variating (V) according to the workability. | 25% C V | 187.75 | 14.5 | 8.4 |

From the mixtures with w/b-ratio=0.5 a decrease in the average flow values were seen. This corresponded to the observations made in the SEM analysis of the morphology of DA consisting of angular particles. Angular particles required more water compared to round particles, thus more water was needed to the mixture in order to obtain a satisfying workability.

The shape and morphology of the DA particles were related to the ash production (firing) conditions where industrial firing conditions of DA similar to spherical coal fly ash particles, may result in a lower water consumption due to spherical particles.

Mixtures with w/b-ratio=0.5 were first conducted and created the basis for the variating w/b-ratios. From Table 12, a decrease of the average flow value of approximately 1% pr. 1% DA replaced with cement for the mixtures with w/b-ratio=0.5 was seen. Thus, an increase in the water content with 1% pr. 1% DA replaced with cement was expected to facilitate average flow values closer to the average flow value for 0% C 0.5. This resulted in the flowing equations used to determine the mix design for mixtures with variating w/b-ratios $$\text{water content}_{5\% C} = 225 + \left(\frac{225}{100} \cdot 5\right) = 236.25g$$

$$\text{water content}_{10\% C} = 225 + \left(\frac{225}{100} \cdot 10\right) = 247.5g$$

$$\text{water content}_{25\% C} = 225 + \left(\frac{225}{100} \cdot 25\right) = 281.25g$$

The determined variating w/b-ratio facilitated an average flow value much closer to 0% C 0.5 for all mixtures, see Table 12.

These two approaches, one constant and one with variating w/b-ratio, made it possible to determine the optimal mix design when DA was utilized as a partial cement replacement in relation to the compressive strength of the cured mortar samples. From Bolomeys formula, an increase in the water content was seen to decrease the compressive strength. However, the Bolomey formula did not consider the absorption of an added admixture, thus did not take into account the actual amount of free water available for the hydration process between water and cement. Therefore, an increase in the amount of water in the mix design does not necessarily lead to a decrease in the compressive strength of the cured mortar samples. A mixture with the appropriate amount of water could facilitate a more appropriate amount of free water available for the hydration process and further facilitate a better workability, making it easier to place and compact the mixture, which also influences the compressive strength. This will be further evaluated subsequently.

Setting Process

Figure 10:
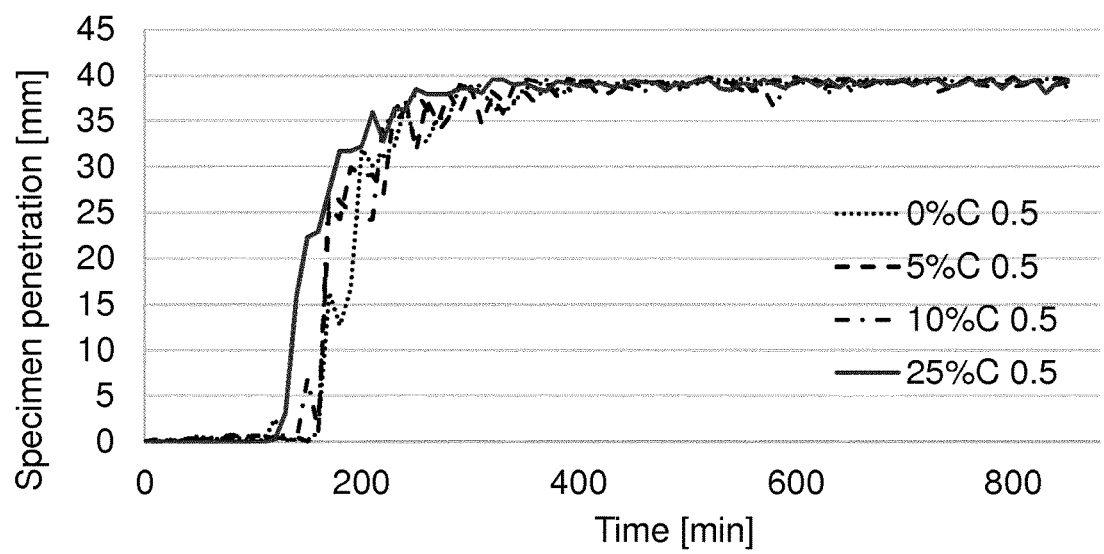
FIG. 10. Setting process for mixtures with water to binder ratio w/b=0.5.

FIG. 9 and FIG. 10 displayed the setting process for 0% C 0.5, 5% C 0.5, 10% C 0.5, 25% C 0.5 and 0% V, 5% C V, 10% C V, 25% C V, respectively.

Setting Process for Mixtures with Varying Water to Binder Ratio w/b=V and 0% Cement Replacement with Water to Binder Ratio w/b=0.5 (0% C 0.5).

FIG. 9 and FIG. 10 displayed no significant difference in the setting process with or without DA or regardless of water content. Table 13 displayed the initial and final setting for all mixtures and the deviation from 0% C 0.5 for all mixtures containing DA.

TABLE 13

Initial and final setting time for all mixtures.

| Mix design | | Initial setting time [min] | Deviation from 0% C 0.5 [%] | Final setting time [min] | Deviation from 0% C 0.5 [%] |
|---|---|---|---|---|---|
| 0% cement replacement and w/b = 0.5 | 0% C 0.5 | 170 | — | 370 | — |
| 5% cement replacement and w/b = 0.5 | 5% C 0.5 | 170 | 0.0 | 350 | −5.7 |

TABLE 13-continued

Initial and final setting time for all mixtures.

| Mix design | | Initial setting time [min] | Deviation from 0% C 0.5 [%] | Final setting time [min] | Deviation from 0% C 0.5 [%] |
|---|---|---|---|---|---|
| 5% cement replacement and w/b variating (V) | 5% C V | 140 | −21.4 | 350 | −5.7 |
| 10% cement replacement and w/b = 0.5 | 10% C 0.5 | 150 | −13.3 | 370 | 0.0 |
| 10% cement replacement and w/b variating (V) | 10% C V | 150 | −13.3 | 340 | −8.8 |
| 25% cement replacement and w/b = 0.5 | 25% C 0.5 | 140 | −21.4 | 320 | −15.6 |
| 25% cement replacement and w/b variating (V) | 25% C V | 180 | 5.6 | 340 | −8.8 |

Table 13 substantiates that there was no significant difference in the setting process of either of the mixtures. A slight facilitation of the initial setting was seen for all mixtures, except 25% C V, shortening the dormant stage and a slight facilitation of the final setting time was seen for all mixtures, except 10% C 0.5, which facilitated the development of the compressive strength.

Traditionally, an addition of alternative admixtures caused a retardation of the setting process (Kosmatka, S. H., Kerkhoff, B. & Panarese, W. C., 2002. *Design and Control of Concrete Mixtures*, Portland Cement Association), which was not the case when DA was used as a partial cement replacement. As determined by the XRD-analysis of the mineralogy described in Example 2 DA contained anhydrite, which could accelerate the hydration reactions and thus accelerate the setting process (Tzouvalas, G., Dermatas, N. & Tsimas, S., 2004. Alternative calcium sulfate-bearing materials as cement retarders: Part I. Anhydrite. *Cement and Concrete Research*, 34(11), pp. 2113-2118). Further DA could also contain particles acting as nucleation sites and contributing to an acceleration of the hydration reactions and the setting process (Moosberg-Bustnes, H., Lagerblad, B. & Forssberg, E., 2004. The function of fillers in concrete. *Materials and Structures*, 37(266), pp. 74-81).

Water-Saturated Density Development

The water-saturated density was measured for all mixtures at 7 and 28 days of curing, right after the specimens were raised from the water bath used for curing and before testing of tensile and compressive strength.

Table 14 displays the measured water-saturated density of the mortar specimens.

TABLE 14

Water-saturated density of mortar specimens at 7 and 28 days of curing.

| | | Water-saturated density [kg/m$^3$] | |
|---|---|---|---|
| Mix design | Specimen | 7 days of curing | 28 days of curing |
| 0% cement replacement and w/b = 0.5 | 0% C 0.5 | 2255.2 ± 11.9 | 2299.3 ± 13.6 |
| 5% cement replacement and w/b = 0.5 | 5% C 0.5 | 2246.3 ± 14.0 | 2271.2 ± 39.0 |
| 5% cement replacement and w/b variating (V) | 5% C V | 2244.6 ± 7.3 | 2256.9 ± 37.9 |
| 10% cement replacement and w/b = 0.5 | 10% C 0.5 | 2223.3 ± 20.6 | 2244.6 ± 18.0 |
| 10% cement replacement and w/b variating (V) | 10% C V | 2233.1 ± 10.3 | 2247.5 ± 4.2 |
| 25% cement replacement and w/b = 0.5 | 25% C 0.5 | 2216.1 ± 15.6 | 2243.0 ± 19.9 |
| 25% cement replacement and w/b variating (V) | 25% C V | 2168.7 ± 37.5 | 2155.3 ± 12.5 |

Addition of a mineral admixture in general decreased the density of a mortar specimen with an increase in the replacement rate of cement with a mineral admixture (Demirboga, R., 2003. Influence of mineral admixtures on thermal conductivity and compressive strength of mortar. *Energy and Buildings*, 35(2), pp. 189-192). The same tendency was seen when DA was used as a partial cement replacement. The reduction of the density was indicated by Fu, X. & Chung, D. D. L., 1997 (Effects of silica fume, latex, methylcellulose, and carbon fibers on the thermal conductivity and specific heat of cement paste. *Cement and Concrete Research*, 27(12), pp. 1799-1804) to be a result of a higher air content in the mixture, which increases with replacement rate. The density increased over time due to development of hydration products, filling the voids in the specimens and increasing the compressive strength.

Tensile Strength Development

The tensile strength of mortar specimens at 7 and 28 days of curing is displayed in Table 15.

TABLE 15

Tensile strength of mortar specimens at 7 and 28 days of curing.

| | | Tensile strength | [MPa] |
|---|---|---|---|
| Mix design | Specimen | 7 days of curing | 28 days of curing |
| 0% cement replacement and w/b = 0.5 | 0% C 0.5 | 7.8 ± 0.1 | 9.4 ± 0.3 |
| 5% cement replacement and w/b = 0.5 | 5% C 0.5 | 8.4 ± 0.3 | 9.2 ± 0.3 |
| 5% cement replacement and w/b variating (V) | 5% C V | 8.2 ± 0.2 | 8.4 ± 0.1 |
| 10% cement replacement and w/b = 0.5 | 10% C 0.5 | 8.7 ± 0.2 | 8.7 ± 0.2 |

TABLE 15-continued

Tensile strength of mortar specimens at 7 and 28 days of curing.

| | | Tensile strength [MPa] | |
|---|---|---|---|
| Mix design | Specimen | 7 days of curing | 28 days of curing |
| 10% cement replacement and w/b variating (V) | 10% C V | 7.5 ± 0.6 | 8.7 ± 0.1 |
| 25% cement replacement and w/b = 0.5 | 25% C 0.5 | 7.4 ± 0.4 | 7.4 ± 0.4 |
| 25% cement replacement and w/b variating (V) | 25% C V | 5.5 ± 0.2 | 7.0 ± 0.4 |

As seen from Table 15, the tensile strength decreased with an increase in the replacement ratio and a variating w/b-ratio facilitated a higher tensile strength over time.

Compressive Strength Development

The compressive strength of mortar specimens at 7 and 28 days of curing are displayed in Table 16.

TABLE 16

Compressive strength of mortar specimens at 7 and 28 days of curing.

| | | Compressive strength [MPa] | |
|---|---|---|---|
| Mix design | Abbrev. | 7 days of curing | 28 days of curing |
| 0% cement replacement and w/b = 0.5 | 0% C 0.5 | 53.5 ± 2.8 | 60.9 ± 3.2 |
| 5% cement replacement and w/b = 0.5 | 5% C 0.5 | 53.6 ± 1.1 | 52.6 ± 3.0 |
| 5% cement replacement and w/b variating (V) | 5% C V | 48.6 ± 1.4 | 55.6 ± 3.9 |
| 10% cement replacement and w/b = 0.5 | 10% C 0.5 | 37.3 ± 1.9 | 45.4 ± 3.8 |
| 10% cement replacement and w/b variating (V) | 10% C V | 49.1 ± 2.0 | 57.1 ± 4.6 |
| 25% cement replacement and w/b = 0.5 | 25% C 0.5 | 43.3 ± 0.8 | 55.5 ± 1.6 |
| 25% cement replacement and w/b variating (V) | 25% C V | 26.7 ± 1.2 | 35.4 ± 0.6 |

Addition of DA reduced the compressive strength, as displayed in Table 16. The addition of extra water in specimens with w/b-ratio=V resulted in a further decrease of the compressive strength at 7 days of curing, as was expected from Bolomeys formula. However, the specimens with w/b-ratio also experienced the highest increase in the compressive strength from 7 to 28 days, with the compressive strength of the specimens 5% C V and 10% C V exceeding the compressive strength of the specimens 5% C 0.5 and 10% C 0.5. This could indicate a lack of free water in specimens with w/b-ratio=0.5, decreasing the amount of CSH-gel formed through pozzolanic reactions, developing at 28 days of curing and onwards. The low values obtained for 25% C V could indicate an exceeding of the optimal DA to cement to water ratio.

5% C 0.5 at 7 days of curing obtained the same compressive strength as 0% C 0.5, substantiating some contribution from the filler effect and/or the particles acting as nucleation site for the cement grains. Both of these phenomena facilitate the compressive strength at an early age and are excepted to contribute in these experiments.

Coefficient of Activity for DA

The coefficient of activity for DA was calculated and displayed in Table 17. A high coefficient of activity corresponded to a high contribution to the compressive strength improving the compressive strength of the cured mortar specimens.

TABLE 17

Coefficient of activity for DA at 7 and 28 days of curing.

| Mix design | Abbrev. | 7 days of curing | 28 days of curing |
|---|---|---|---|
| 5% cement replacement and w/b = 0.5 | 5% C 0.5 | 9.35 | 3.54 |
| 10% cement replacement and w/b = 0.5 | 10% C 0.5 | 4.13 | 2.77 |
| 25% cement replacement and w/b = 0.5 | 25% C 0.5 | 1.31 | 1.03 |
| 5% cement replacement and w/b variating (V) | 5% C V | 8.78 | 6.24 |
| 10% cement replacement and w/b variating (V) | 10% C V | 4.23 | 3.93 |
| 25% cement replacement and w/b variating (V) | 25% C V | 1.28 | 1.20 |

As displayed in Table 17, the coefficient of activity varied significantly. Bolomey's formula described the coefficient of activity as a constant, only depending on substitution type, however Khokhar, M. I. A. et al., 2010 (Mix design of concrete with high content of mineral additions: Optimisation to improve early age strength. Cement and Concrete Composites, 32(5), pp. 377-385) has investigated several mineral additives and concluded the coefficient of activity to be depended on both time, substitution type and substitution rate. All calculated coefficients of activity were seen to follow the tendency of decreasing with replacement rate and over time, but all arrive above the traditional interval for coal fly ash of 0.3-0.5 (Herholdt, A. D. et al., 1985. Beton-Bogen (In Danish). Cementfabrikkernes tekniske oplysningskontor, Aalborg Portland, 2; DS/EN 206-1 2002).

Figure 11:
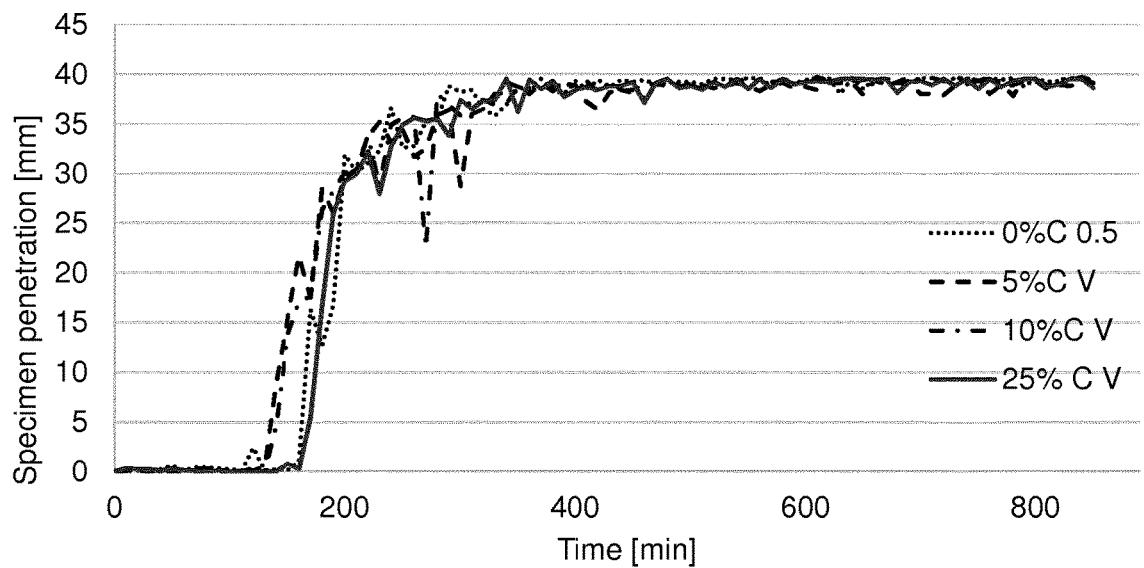
FIG. 11. Setting process for mixtures with variating water to binder ratio w/b=V and 0% cement replacement and w/b=0.5 (0% C 0.5).

The theoretical compressive strengths according to Bolomey's formula with a coefficient of activity of 0.5 was calculated and compared to the empirical obtained compressive strengths for all specimens, see FIG. 11. From FIG. 11, DA was substantiated to contribute significantly more to the compressive strength compared to the calculated, theoretical values for coal fly ash.

Strength Activity Index

The compressive strength of the mortar specimens 0% C 0.5, 25% C 0.5 and 25% C V at 28 and 90 days of curing is displayed in Table 18.

TABLE 18

Compressive strength of mortar specimens with 0% and 25% cement replacement at 28 and 90 days of curing.

| | | Compressive strength [MPa] | |
|---|---|---|---|
| Mix design | Abbrev. | 28 days of curing | 90 days of curing |
| 0% cement replacement and w/b = 0.5 | 0% C 0.5 | 60.9 ± 3.2 | 67.2 ± 2.9 |
| 25% cement replacement and w/b = 0.5 | 25% C 0.5 | 55.5 ± 1.6 | 59.1 ± 2.7 |
| 25% cement replacement and w/b variating (V) | 25% C V | 35.4 ± 0.6 | 40.5 ± 2.7 |

Figure 12:
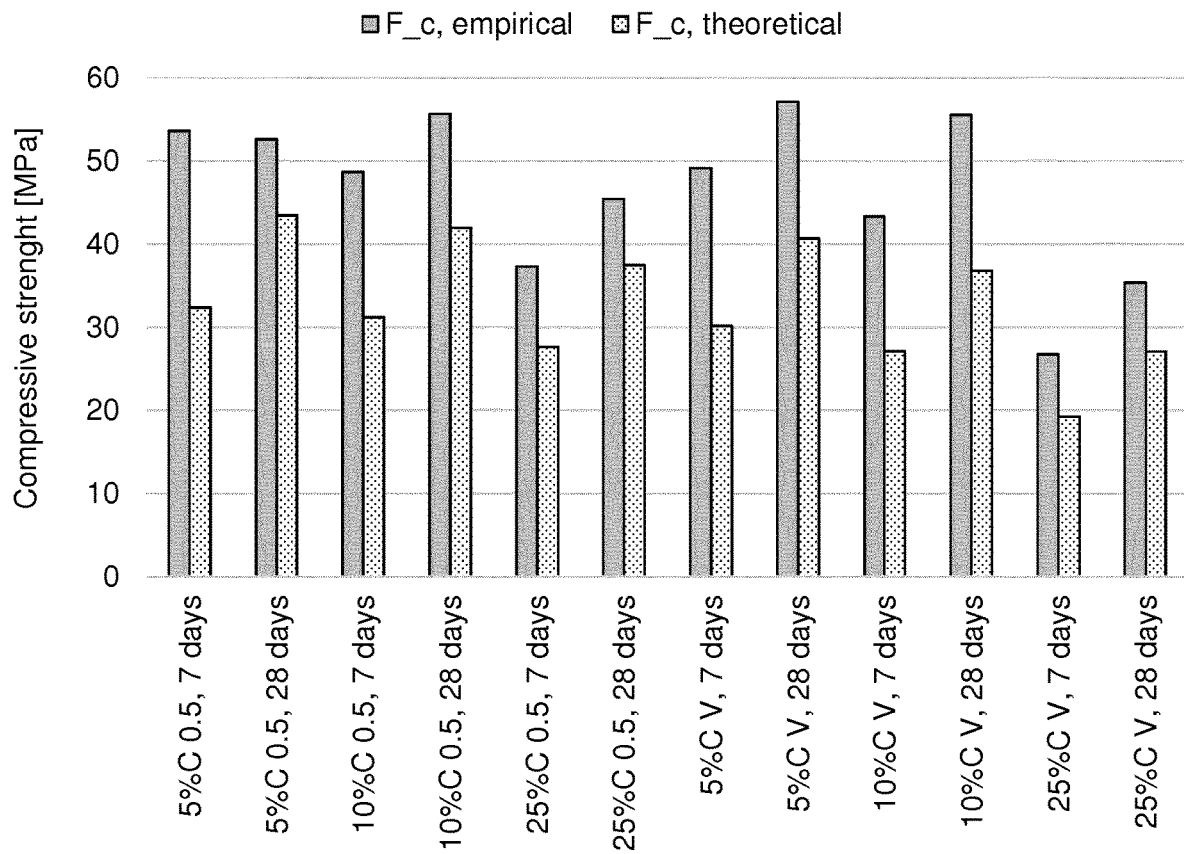
FIG. 12. Empirical and theoretical compressive strength (coefficient of activity=0.5, calculated according to Bolomey's formula).

FIG. 12 shows a bar chart for the normalized compressive strength for 0% C 0.5, 25% C 0.5 and 25% C V at 28 and 90 days of curing.

TABLE 19

Strength activity index for mortar specimens with 25% cement replacement with water to binder ratio w/b = 0.5 and variating, respectively, at 28 and 90 days of curing, including deviation from limits according to (DS/EN 450-1 2012).

| Specimen | SAI at 28 days of curing [%] | Deviation from limit, 28 days [%] | SAI at 90 days of curing [%] | Deviation from limit, 90 days [%] |
|---|---|---|---|---|
| 25% C 0.5 | 74.61 | −0.39 | 87.91 | 2.91 |
| 25% C V | 58.11 | −16.89 | 60.28 | −24.72 |

According to (DS/EN 450-1 2012) the compressive strength of a specimen with a 25% replacement of cement with a mineral admixture should not be less than 75% and 85% of the compressive strength of a control specimen at 28 and 90 days of curing, respectively if pozzolanic activity is present. Table 19 displays the calculated strength activity index for the mortar specimens 25% C 0.5 and 25% C V and the deviation from the 75% and 85% limits. As 25% C 0.5 arrived at a strength activity index 0.39% at 28 days of curing below the limit at 28 days of curing and at 2.91% above the limit at 90 days, digestate ash can be categorized as a pozzolan according to the strength activity index, contributing to the compressive strength. 25% C V arrives at significantly lower results for the strength activity index. This is due to a significant increase in the water content of the mixture leading to a decrease in the compressive strength, expected from Bolomey's formula.

Digestate-ash arrived at a content of primary oxides below the limit of 70% set by (ASTM International C618-15 2010), necessary in order for an admixture to be categorized as a pozzolan. This substantiates the conclusions proposed in the previous section of the digestate-ash contribution to both the filler effect and/or the particles acting as nucleation site for the cement grains, alongside contributing to the pozzolanic activity, all factors which improve the compressive strength of the mortar samples.

Example 5. Preparation of Lightweight Aggregates

In this example, it was investigated if the organic matter in the DD and SS have characteristics as foaming agents (after Franus, M., Barnat-Hunek, D. & Wdowin, M., 2016. Utilization of sewage sludge in the manufacture of lightweight aggregate. *Environmental Monitoring and Assessment*, 188(1), p. 10), where LWAs were produced from clay and sewage sludge.

Additives, which cause the foaming or bloating of the material should be added in order to increase porosity (Ducman, V. & Mirtič, B., 2009. The applicability of different waste materials for the production of lightweight aggregates. *Waste Management*, 29(8), pp. 2361-2368). Foaming agents, which generate gaseous bubbles to bloat the body of ceramics, may be classified into organic foaming agents and inorganic foaming agents. Normally, inorganic foaming agents are $Fe_2O_3$, sulfate, carbonates, water-glass, $MnO_2$, and SiC (Yue, M. et al., 2012. Properties and effect of forming sewage sludge into lightweight ceramics. *Frontiers of Environmental Science & Engineering*, 6(1), pp. 117-124). Both inorganic and organic foaming agents can expand the LWA during the sintering process, but their effects on expansion are different (Yue, M. et al., 2012. Properties and effect of forming sewage sludge into lightweight ceramics. *Frontiers of Environmental Science & Engineering*, 6(1), pp. 117-124).

Determination of the mix designs for mixtures containing dewatered YBC and dried digestate were based on the results for the liquid and plastic limits ($w_L$ and $w_P$ respectively) determined by the Atterberg limits.

Mix designs were made with replacement ratios of 0%, 10% and 30% with dried digestate. LWAs were formed by hand to spheres of 1.5 cm. For comparison LWAs were produced with SS. The mix design for production of approximate 100 pcs is given in Table 20. The YBC, DD and SS were all dried at 105 degrees C. and subsequently milled to a particle size<0.5 mm prior to forming the LWA.

TABLE 20

Mix design for production of approximate 30 pcs LWA-1 (YBC: Yellow brick clay, DD: Dewatered digestate, SS: Dewatered digestate and Water: Demineralized water).

| Abbreviation | YBC [g] | DD [g] | SS [g] | Water [g] | Initial water content [% dry weight] |
|---|---|---|---|---|---|
| YBC 0% DD | 100 | | | 21.93 | 17.99 |
| YBC 10% DD | 90 | 10 | | 28.11 | 21.94 |
| YBC 30% DD | 70 | 30 | | 41.97 | 29.56 |
| YBC 10% SS | 90 | | 10 | 28.11 | 21.94 |
| YBC 30% SS | 70 | | 30 | 41.97 | 29.56 |

YBC was used in this work as a non-expansive clay, making the effect of the addition of digestate more obvious.

The method for production of LWA was in accordance with (Franus, M., Barnat-Hunek, D. & Wdowin, M., 2016. Utilization of sewage sludge in the manufacture of lightweight aggregate. *Environmental Monitoring and Assessment*, 188(1), p. 10), where sewage sludge was used. The dry materials (dried and milled YBC or KA and dried and milled digestate) were placed in a bowl and mixed. Water was added to meet the specification displayed in Table 20. The mixing was performed in a mechanic mixer. Three spheres of each mix were formed by hand. The diameter was approximately 15 mm.

The burning of LWAs followed:
- 40 degrees C. for 2 hours
- 60 degrees C. for 2 hours
- 110 degrees C. for 2 hours
- 1150 degrees C. for 30 min (The increase in temperature was 5 degrees C./min)

After sintering, the LWA was left in the oven to cool down to a temperature of 100 degrees C. before the LWA was removed to a desiccator to room temperature.

Results

By visual inspection of the produced LWAs with DD or SS clear size differences were seen, and the LWA with DD was clearly larger than the LWAs with SS. Also the colour differed. The LWAs with DD were yellow and the LWAs with SS were reddish. This difference was most likely attributed to a high content of Fe in the SS from the salts used to precipitate phosphorous at the wastewater treatment plant.

Figure 13:
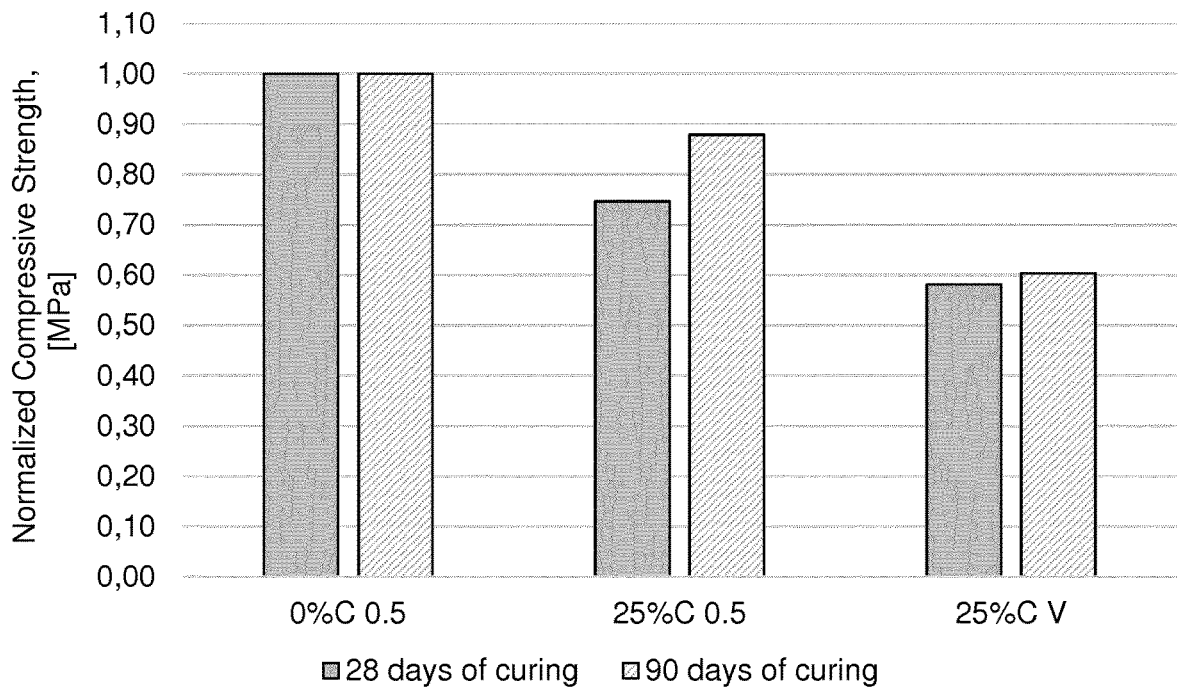
FIG. 13 Normalized compressive strength of mortar specimens with 25% cement replacement at 28 and 90 days of curing.

The diameter, when forming the clay by hand was approximately 15 mm, and neither of the spheres were expanded (FIG. 13). Actually, on the contrary, the spheres with DD and SS had decreased diameters after firing. The diameter of the LWAs with SS had decreased the most in diameter compared to the LWAs with DD. The decrease in diameter for the LWAs with SS and DD must be related to decomposition of the organic matter from the SS and DD. The organic matter content (LoI at 550 degrees C.) was: DD 59.7% and SS 63.4%. The difference in organic matter alone, cannot explain the difference between the diameter of 10.8 mm and 13.9 mm in the two types of spheres with 30% clay replacement. The TGA results indicated that the type of organics differed in the two samples, especially >400 degrees C., which are the non-biodegradable organics and there seems to be more in this category in the DD than in the SS.

Figure 14:
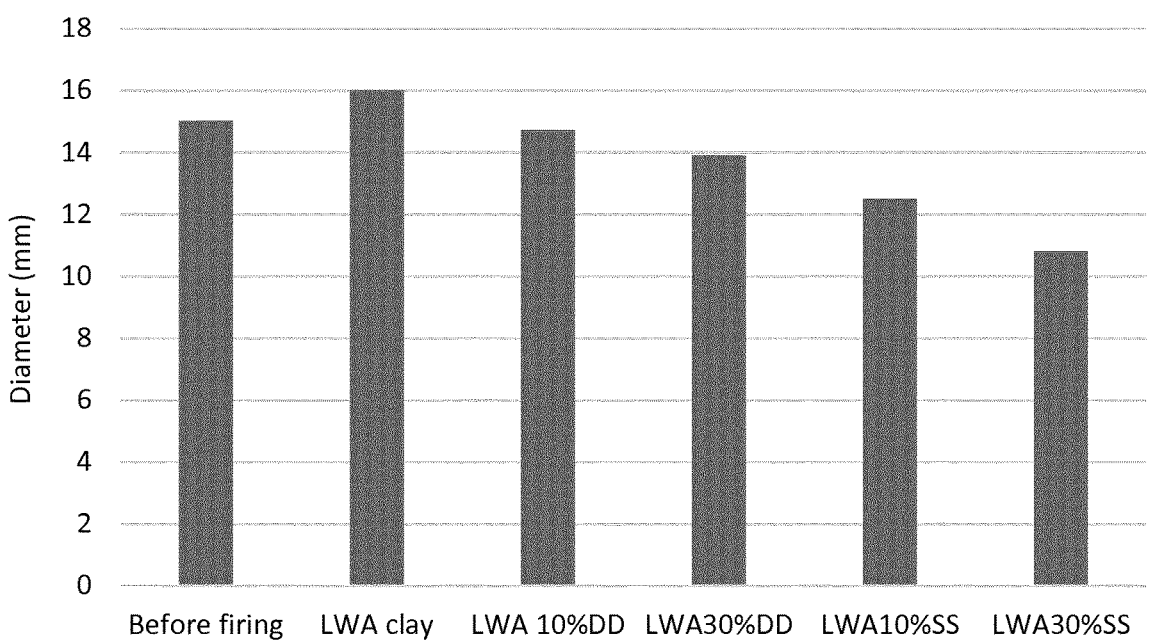
FIG. 14. Diameter of spherical LWAs (lightweight aggregates).
Figure 15:
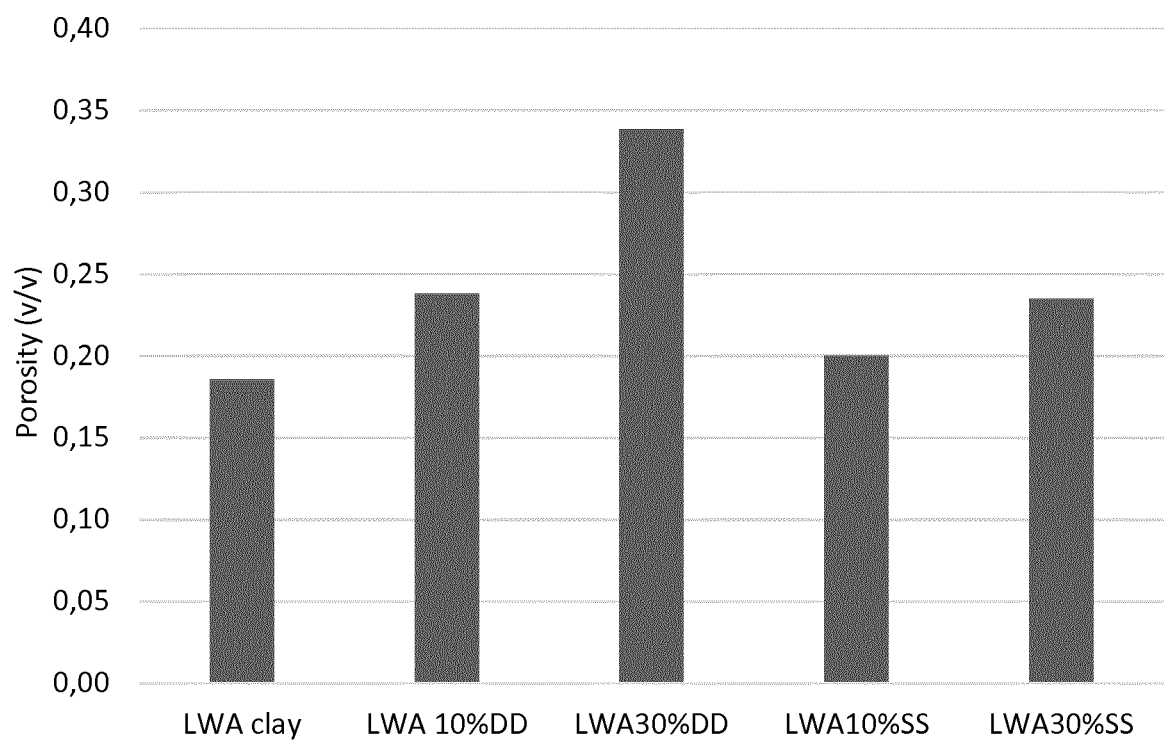
FIG. 15. Porosity of the fired spheres of LWAs (lightweight aggregates).

The porosity of the spheres is seen in FIG. 14. The porosity was highest for the LWAs with DD, with the highest porosity with the highest clay replacement with DD (30%). In these spheres, the porosity was 0.34 compared to 0.19 for the spheres from clay alone. The porosity of the spheres with SS was only slightly increased compared to the porosity of the spheres of pure clay.

Thus, there was a clear difference in porosity of the fired spheres with SS and DD.

The invention claimed is:

1. A process for manufacture of a building material comprising the steps of:
    mixing clay and/or sand with from 1% w/w to 30% w/w of a dewatered digestate, dried digestate, or digestate ash obtained from Municipal Solid Waste (MSW) on a dry weight basis,
    optionally adjusting the water content of the mixture,
    shaping the mixture,
    drying the shaped mixture, and
    optionally firing the shaped mixture,
    so as to form said building material; wherein the dewatered digestate, dried digestate, or digestate ash is obtained from MSW by a process comprising liquefaction of the organic fraction of MSW by addition of one or more enzymes to form a bioliquid, anaerobic digestion of the bioliquid, and isolation of dewatered digestate from the anaerobic digestion of the bioliquid, and optionally drying of the dewatered digestate to form dried digestate or optionally burning of the dewatered digestate or the dried digestate to form digestate ash.

2. The process according to claim 1, wherein said building material is selected from the group consisting of bricks, light weight aggregates, tiles, floor tiles, roof tiles, wall tiles, drain pipes, sewer pipes, ducts, field drains, clay blocks, pavers, cement, concrete and mortar.

3. The process according to claim 1, wherein said dewatered digestate, dried digestate, or digestate ash is dewatered digestate and has a moisture content of at least 10% w/w.

4. The process according to claim 1, wherein said dewatered digestate, dried digestate, or digestate ash is dewatered digestate and has a moisture content in the range from about 65% w/w to about 75% w/w.

5. The process according to claim 1, wherein said dewatered digestate, dried digestate, or digestate ash has a content of organic matter in the range from about 45% w/w to about 75% w/w on dry weight basis.

6. The process according to claim 1, wherein said dewatered digestate, dried digestate, or digestate ash has a content of inorganic matter in the range from about 25% w/w to about 55% w/w on dry weight basis.

7. The process according to claim 1, wherein the process comprises firing the shaped mixture at a temperature from about 900 degrees C. to about 1200 degrees C.

8. A building material characterized in being manufactured by the process according to claim 1.

9. The building material according to claim 8 which has been manufactured by a process where the total amount of raw materials comprises from 5% w/w to 30% w/w dewatered digestate, dried digestate, or digestate ash on dry weight basis.

10. The building material according to claim 8, wherein the building material is selected from the group consisting of bricks, light weight aggregates, tiles, floor tiles, roof tiles, wall tiles, drain pipes, sewer pipes, ducts, field drains, clay blocks, and pavers.

11. A brick characterized in being manufactured by the process according to claim 1.

12. The brick of claim 11, wherein the clay and/or sand is clay, and wherein the clay and the dewatered digestate, dried digestate, or digestate ash are mixed at a ratio of 70-90% clay and 10-30% dewatered digestate, dried digestate, or digestate ash w/w on a dry weight basis.

13. A light weight aggregate characterized in being manufactured by a process according to claim 1.

14. A material selected from concrete, a concrete additive, cement or mortar characterized in being manufactured by the process according to claim 1.

15. The material of claim 14, wherein the clay and/or sand and the dewatered digestate, dried digestate, or digestate ash are mixed at a ratio of 75-90% clay and/or sand to 10-25% dewatered digestate, dried digestate, or digestate ash w/w on a dry weight basis.

16. The process according to claim 1, wherein the dewatered digestate, dried digestate, or digestate ash has a lower phosphor content than a digestate obtained from sewage sludge.

17. The process according to claim 1, wherein the dewatered digestate, dried digestate, or digestate ash is dewatered digestate and has a moisture content of 25-30% w/w.

18. The process according to claim 1, wherein the dewatered digestate, dried digestate, or digestate ash is dried digestate, wherein the dried digestate is obtained from dewatered digestate by a process comprising drying of dewatered digestate followed by milling the dried digestate to a particle size of less than 0.5 mm.

19. The process according to claim 1, wherein the dewatered digestate, dried digestate, or digestate ash is digestate ash, wherein the digestate ash is obtained from dewatered digestate by a process comprising drying of dewatered digestate to form dried digestate followed by milling the dried digestate to a particle size of less than 0.5 mm, followed by burning the milled, dried digestate to produce digestate ash.

20. The process of claim 19, wherein the digestate ash has a pH of at least 11.5, and/or a conductivity lower than coal fly ash (CFA), and/or a water solubility lower than CFA.

* * * * *